(12) United States Patent
Naumann et al.

(10) Patent No.: US 9,440,220 B2
(45) Date of Patent: *Sep. 13, 2016

(54) SUPERABSORBENT POLYMER WITH CROSSLINKER

(75) Inventors: Matthias Naumann, Greensboro, NC (US); Stanley A. McIntosh, Greensboro, NC (US); Frank Schubert, Neukirchen-Vluyn (DE); Christoph Loick, Tonisvorst (DE)

(73) Assignee: Evonik Corporation, Parsippany, NJ (US)

( * ) Notice: Subject to any disclaimer, the term of this patent is extended or adjusted under 35 U.S.C. 154(b) by 138 days.

This patent is subject to a terminal disclaimer.

(21) Appl. No.: 14/354,372

(22) PCT Filed: Dec. 30, 2011

(86) PCT No.: PCT/US2011/068143
§ 371 (c)(1),
(2), (4) Date: Oct. 20, 2014

(87) PCT Pub. No.: WO2013/101197
PCT Pub. Date: Jul. 4, 2013

(65) Prior Publication Data
US 2015/0093575 A1    Apr. 2, 2015

(51) Int. Cl.
| | |
|---|---|
| *B01J 20/26* | (2006.01) |
| *C08F 220/06* | (2006.01) |
| *A61L 15/24* | (2006.01) |
| *A61L 15/60* | (2006.01) |
| *A61F 13/53* | (2006.01) |
| *B01J 20/28* | (2006.01) |
| *B01J 20/30* | (2006.01) |
| *C08F 222/10* | (2006.01) |
| *A61F 13/15* | (2006.01) |

(52) U.S. Cl.
CPC .............. *B01J 20/267* (2013.01); *A61F 13/53* (2013.01); *A61L 15/24* (2013.01); *A61L 15/60* (2013.01); *B01J 20/28016* (2013.01); *B01J 20/28026* (2013.01); *B01J 20/3028* (2013.01); *B01J 20/3085* (2013.01); *C08F 220/06* (2013.01); *A61F 2013/15463* (2013.01); *A61F 2013/530299* (2013.01); *B01J 2220/445* (2013.01); *B01J 2220/68* (2013.01); *C08F 222/1006* (2013.01); *Y10T 428/2982* (2015.01); *Y10T 428/31855* (2015.04)

(58) Field of Classification Search
CPC .......... C08F 220/06; C08F 222/1006; A61L 15/24; A61L 15/60; B01J 20/3085; B01J 20/3028; B01J 20/28026; B01J 20/28016; B01J 2220/445; B01J 20/267; B01J 2220/68; A61F 13/53; Y10T 428/31855; Y10T 428/2982

USPC ................. 428/402, 500; 502/402; 525/385; 604/368
See application file for complete search history.

(56) References Cited

U.S. PATENT DOCUMENTS

| | | | |
|---|---|---|---|
| 6,087,450 A * | 7/2000 | Breitbach | A61L 15/60 525/242 |
| 6,716,929 B2 | 4/2004 | Wilson | |
| 7,173,086 B2 | 2/2007 | Smith et al. | |
| 7,285,614 B2 | 10/2007 | Jonas et al. | |
| 7,777,093 B2 | 8/2010 | Smith et al. | |
| 7,812,082 B2 | 10/2010 | McIntosh et al. | |
| 8,071,202 B2 | 12/2011 | Furno et al. | |
| 8,236,884 B2 | 8/2012 | Smith et al. | |
| 8,247,499 B2 | 8/2012 | Walden et al. | |
| 8,420,567 B1 * | 4/2013 | Naumann | A61L 15/60 502/401 |
| 8,476,189 B1 * | 7/2013 | Naumann | A61L 15/60 502/404 |
| 8,519,041 B2 | 8/2013 | Smith et al. | |
| 8,552,134 B2 * | 10/2013 | Fujimaru | C08F 220/06 526/318 |
| 8,952,116 B2 * | 2/2015 | Kobayashi | C08K 5/098 524/437 |
| 9,090,718 B2 * | 7/2015 | Sakamoto | C08F 2/44 |
| 2008/0280128 A1 | 11/2008 | Furno et al. | |
| 2009/0105389 A1 | 4/2009 | Walden et al. | |
| 2009/0227741 A1 | 9/2009 | Walden et al. | |

(Continued)

FOREIGN PATENT DOCUMENTS

| | | |
|---|---|---|
| DE | 102005018924 A1 | 10/2006 |
| JP | 2000-501437 A | 2/2000 |

(Continued)

OTHER PUBLICATIONS

Written Opinion mailed on Jul. 10, 2014 in PCT/US2011/068143 (4 pages).

(Continued)

*Primary Examiner* — Leszek Kiliman
(74) *Attorney, Agent, or Firm* — Bernard Lau; Linda S. Li; Jason S. Ngui

(57) ABSTRACT

The present invention further relates to a particulate superabsorbent polymer composition comprising a crosslinker composition that is the reaction product selected from (i) saturated amines and/or saturated polyamines with ethylenically unsaturated glycidyl compounds and/or ethylenically unsaturated polyglycidyl compounds, (ii) ethylenically unsaturated amines and/or ethylenically unsaturated polyamines with saturated glycidyl compounds and/or saturated polyglycidyl compounds, or (iii) ethylenically unsaturated amines and/or ethylenically unsaturated polyamines with ethylenically unsaturated glycidyl compounds and/or ethylenically unsaturated polyglycidyl compounds; and a surface crosslinking agent applied to the particle surface. The present invention further relates to an absorbent article that includes such particulate superabsorbent polymer compositions.

40 Claims, 4 Drawing Sheets

(56) References Cited

U.S. PATENT DOCUMENTS

| | | |
|---|---|---|
| 2011/0224361 A1 | 9/2011 | Daniel et al. |
| 2012/0145956 A1 | 6/2012 | Walden et al. |
| 2013/0253158 A1 | 9/2013 | Naumann et al. |
| 2013/0310251 A1 | 11/2013 | Smith et al. |
| 2014/0031498 A1 | 1/2014 | Smith et al. |
| 2014/0045683 A1 | 2/2014 | Loick et al. |
| 2014/0054497 A1 | 2/2014 | Wattebled et al. |

FOREIGN PATENT DOCUMENTS

| | | |
|---|---|---|
| WO | 2004096304 A1 | 11/2004 |
| WO | 2005025628 A1 | 3/2005 |
| WO | 2005044900 A1 | 5/2005 |
| WO | 2007070776 A2 | 6/2007 |
| WO | 2008118237 A1 | 10/2008 |
| WO | 2009080611 A2 | 7/2009 |
| WO | 2010057912 A1 | 5/2010 |

OTHER PUBLICATIONS

Buchholz, Frederick L. and Graham, Andrew T., "Modern Superabsorbent Polymer Technology," copyright 1998, John Wiley & Sons, Inc., Chapter 1: "Absorbency and Superabsorbency," pp. 1-17 (19 pages).

Buchholz, Frederick L. and Graham, Andrew T., "Modern Superabsorbent Polymer Technology," copyright 1998, John Wiley & Sons, Inc., Chapter 2: "Chemistry of Superabsorbent Polyacrylates," pp. 19-67 (51 pages).

Buchholz, Frederick L. and Graham, Andrew T., "Modern Superabsorbent Polymer Technology," copyright 1998, John Wiley & Sons, Inc., Chapter 3: "Commercial Processes for the Manufacture of Superabsorbent Polymers," pp. 69-117 (51 pages).

Buchholz, Frederick L. and Graham, Andrew T., "Modern Superabsorbent Polymer Technology," copyright 1998, John Wiley & Sons, Inc., Chapter 4: "Analysis and Characterization of Superabsorbent Polymers," pp. 119-165 (49 pages).

Buchholz, Frederick L. and Graham, Andrew T., "Modern Superabsorbent Polymer Technology," copyright 1998, John Wiley & Sons, Inc., Chapter 5: "The Structure and Properties of Superabsorbent Polyacrylates," pp. 167-221 (57 pages).

Henn et al., U.S. Appl. No. 14/352,171, filed Apr. 16, 2014.

International Search Report mailed on Aug. 15, 2012 in PCT/US2011/068143 (3 pages).

Wattebled et al., U.S. Appl. No. 14/352,091, filed Apr. 16, 2014.

\* cited by examiner

SUPERABSORBENT POLYMER WITH CROSSLINKER

This application is a national stage application under 35 U.S.C. §371 of International Application No. PCT/US2011/068143 filed 30 Dec. 2011, the disclosures of which are expressly incorporated herein by reference.

BACKGROUND

The present invention is directed towards a superabsorbent polymer, particulate superabsorbent polymer compositions, and methods to make such products and absorbent articles containing such products. Examples of superabsorbent polymer may include a crosslinked partially neutralized polymer, including crosslinked polyacrylic acids or crosslinked starch-acrylic acid graft polymers, that is capable of absorbing large amounts of aqueous liquids and body fluids, such as urine or blood, with swelling and the formation of hydrogels, and of retaining the aqueous liquids under a certain pressure in accordance with the general definition of superabsorbent polymer. Superabsorbent polymer may be formed into particles, generally referred to as particulate superabsorbent polymer, wherein the particulate superabsorbent polymer may be post-treated with surface crosslinking, surface treatment, and other treatment to form particulate superabsorbent polymer compositions. The acronym SAP may be used in place of superabsorbent polymer, superabsorbent polymer composition, and particles hereof. A primary use of superabsorbent polymer and superabsorbent polymer compositions is in sanitary articles, such as babies' diapers, incontinence products, or sanitary towels. A comprehensive survey of superabsorbent polymers, and their use and manufacture, is given in F. L. Buchholz and A. T. Graham (editors) in "Modern Superabsorbent Polymer Technology," Wiley-VCR, New York, 1998.

Superabsorbent polymers may be prepared by initially neutralizing unsaturated carboxylic acids or derivatives thereof, such as acrylic acid, alkali metal (e.g., sodium and/or potassium) or ammonium salts of acrylic acid, alkyl acrylates, and the like in the presence of a caustic treatment, such as sodium hydroxide, and then polymerizing the product with a relatively small amount of an internal, or monomer, crosslinker such as a di- or poly-functional monomer. The di- or poly-functional monomer materials may serve as covalent internal crosslinking agents to lightly crosslink the polymer chains, thereby rendering them water-insoluble, yet water-swellable. These lightly crosslinked superabsorbent polymers contain a multiplicity of carboxyl groups attached to the polymer backbone. These carboxyl groups generate an osmotic driving force for the absorption of body fluids by the crosslinked polymer network.

In addition to covalent internal crosslinking agents, ionic internal crosslinking agents have been utilized to prepare superabsorbent polymers. The ionic internal crosslinking agents are generally coordination compounds comprising polyvalent metal cations, such as $Al^{3+}$ and $Ca^{2+}$, as disclosed in U.S. Pat. No. 6,716,929 and U.S. Pat. No. 7,285,614. The superabsorbent polymers disclosed in these patents have a slow rate of absorption, due to the presence of ionic crosslinks. In this context, the absorption rate may be measured by a Vortex Test.

Superabsorbent polymers, useful as absorbents in absorbent articles such as disposable diapers, need to have adequately high absorption capacity, as well as adequately high gel strength. Absorption capacity needs to be sufficiently high to enable the absorbent polymer to absorb significant amounts of the aqueous body fluids encountered during use of the absorbent article. Gel strength relates to the tendency of the swollen polymer particles to deform under an applied stress, and needs to be such that the particles do not deform under pressure, and fill the capillary void spaces in the absorbent member, or article, to an unacceptable degree, so-called gel blocking, thereby inhibiting the rate of fluid uptake, or the fluid distribution, by the member or article. Once gel-blocking occurs, it can substantially impede the distribution of fluids to relatively dry zones or regions in the absorbent article, and leakage from the absorbent article can take place well before the particles of absorbent polymer in the absorbent article are fully saturated, or before the fluid can diffuse or wick past the "blocking" particles into the rest of the absorbent article.

U.S. Pat. No. 6,087,450 is directed to providing internal cross-linking agents and superabsorbent polymers cross-linked with them, as well as a process for their production. These superabsorbent polymers are suitable as superabsorbers in diaper constructions or other technical applications, by using internal cross-linking agents which are characterized by the fact that by means of reacting a glycidyl compound with unsaturated amines, for example, allylamines, they open the epoxide ring, thereby forming a hydroxyl group which is optionally available for a subsequent ethoxylation. There are also other reaction paths to produce the cross-linking agents according to the present invention; for example, reacting amines with unsaturated glycidyl compounds, such as (meth)allyl glycidyl ethers or glycidyl (meth)acrylates.

The characteristic features of superabsorbers can be improved by surface cross-linkage, in particular with respect to their liquid absorption under pressure. During surface cross-linkage the carboxyl groups of the polymer molecules are cross-linked at the surface of the superabsorber particles with cross-linking agents at elevated temperatures. Among others, multivalent metallic salts, glycidyl compounds, polyols, polyepoxides, polyamines, alkylene carbonates, and polyethylene glycols are used as cross-linking agents.

It is the object of the present invention to provide superabsorbent polymer polymers having improved permeability as measured by the Gel Bed Permeability Test, as set forth herein, as well as a process for their production.

SUMMARY

The present invention includes numerous embodiments, of which some are included herein. One embodiment of the present invention is a particulate superabsorbent polymer composition comprising:

a) polymerizable monomer wherein the monomer is selected from unsaturated acid groups-containing monomers, ethylenically unsaturated carboxylic acid anhydride, salts, or derivatives thereof;

b) an internal crosslinker composition that is the reaction product selected from (i) saturated amines and/or saturated polyamines with ethylenically unsaturated glycidyl compounds and/or ethylenically unsaturated polyglycidyl compounds, or (ii) ethylenically unsaturated amines and/or ethylenically unsaturated polyamines with saturated glycidyl compounds and/or saturated polyglycidyl compounds, or (iii) ethylenically unsaturated amines and/or ethylenically unsaturated polyamines with ethylenically unsaturated glycidyl compounds and/or ethylenically unsaturated polyglycidyl compounds; wherein components a) and b) are polymerized and granulated to form particulate superabsorbent polymer having a particle surface wherein at least 40 wt % of the particulate superabsorbent polymer has a particle size from 300 μm to 600 μm; and c) from 0.01 to 5 wt % based on the dry superabsorbent polymer composition weight of a surface crosslinking agent applied to the particle surface;

wherein the particulate superabsorbent polymer composition has a Centrifuge Retention Capacity of from 20 g/g to 40 g/g as determined by the Centrifuge Retention Capacity Test set forth herein, and a gel bed permeability of at least 5 Darcy or more as determined by the Gel Bed Permeability Test set forth herein.

Another embodiment of the current invention is a method to make particulate superabsorbent polymer composition comprising the steps of:

a) preparing a superabsorbent polymer by the process of polymerizing of at least one monomer selected from an ethylenically unsaturated carboxylic acid, ethylenically unsaturated carboxylic acid anhydride, salts or derivatives thereof based on the superabsorbent polymer, and from 0.001% by weight to 1% by weight of an internal crosslinking composition that is the reaction product selected from
  (i) saturated amines and/or saturated polyamines with ethylenically unsaturated glycidyl compounds and/or ethylenically unsaturated polyglycidyl compounds,
  (ii) ethylenically unsaturated amines and/or ethylenically unsaturated polyamines with saturated glycidyl compounds and/or saturated polyglycidyl compounds, or
  (iii) ethylenically unsaturated amines and/or ethylenically unsaturated polyamines with ethylenically unsaturated glycidyl compounds and/or saturated polyglycidyl compounds;

b) polymerizing the superabsorbent polymer;

c) granulating the superabsorbent polymer to form particulate superabsorbent polymer wherein at least 40 wt % of the particulate superabsorbent polymer has a particle size from 300 μm to 600 μm;

d) surface crosslinking the particulate superabsorbent polymer with from 0.001 to 5.0 wt % based on the dry superabsorbent polymer composition powder weight of surface crosslinking agent applied to the particle surface;

e) heat treating the surface crosslinked particulate superabsorbent polymer of step e) at a temperature from 150° C. to 250° C. for 20 to 120 minutes to form surface crosslinked particulate superabsorbent polymer; and wherein the particulate superabsorbent polymer composition has a Centrifuge Retention Capacity of from 20 g/g to 40 g/g as determined by the Centrifuge Retention Capacity Test set forth herein, and a gel bed permeability of at least 5 Darcy or more as determined by the Gel Bed Permeability Test set forth herein.

Another embodiment of the current invention is a method to make a particulate superabsorbent polymer composition comprising the steps of: a) preparing a superabsorbent polymer by the process of polymerizing of at least one monomer selected from an ethylenically unsaturated carboxylic acid, ethylenically unsaturated carboxylic acid anhydride, salts or derivatives thereof based on the superabsorbent polymer and from 0.001% by weight to 1% by weight of an internal crosslinking composition that is the reaction product selected from
  (i) saturated amines and/or saturated polyamines with ethylenically unsaturated glycidyl compounds and/or ethylenically unsaturated polyglycidyl compounds,
  (ii) ethylenically unsaturated amines and/or ethylenically unsaturated polyamines with saturated glycidyl compounds and/or saturated polyglycidyl compounds, or
  (iii) ethylenically unsaturated amines and/or ethylenically unsaturated polyamines with ethylenically unsaturated glycidyl compounds and/or ethylenically unsaturated polyglycidyl compounds;

b) polymerizing the superabsorbent polymer;

c) granulating the superabsorbent polymer to form particulate superabsorbent polymer wherein at least 40 wt % of the particulate superabsorbent polymer has a particle size from 300 μm to 850 μm;

d) surface treating the surface crosslinked particulate superabsorbent polymer of step c) with from 0.01 to 5 wt % based on the dry superabsorbent polymer composition powder weight of an insoluble, inorganic powder and/or from 0.01 to 5 wt % based on the dry superabsorbent polymer composition powder weight of a multivalent metal salt;

e) surface crosslinking the particulate superabsorbent polymer with from 0.001 wt % to 5.0 wt % based on the dry superabsorbent polymer composition weight of surface crosslinking agent applied to the particle surface; and f) heat treating the surface crosslinked particulate superabsorbent polymer of step d) at a temperature from 150° C. to 250° C. for from 20 to 120 minutes to form surface crosslinked particulate superabsorbent polymer; and wherein the particulate superabsorbent polymer composition has a Centrifuge Retention Capacity of 20 g/g to 40 g/g as determined by the Centrifuge Retention Capacity Test set forth herein, and a Gel Bed Permeability of at least 5 Darcy or more as determined by the Gel Bed Permeability Test set forth herein.

Another embodiment of the current invention is an absorbent article absorbent article comprising: (a) a liquid pervious topsheet; (b) a liquid impervious backsheet; (c) a core positioned between (a) and (b), said core comprising 10% to 100% by weight of the particulate superabsorbent polymer composition and 0 wt % to 90 wt % by weight of hydrophilic fiber material; (d) optionally a tissue layer positioned directly above and below said core (c); and (e) optionally an acquisition layer positioned between (a) and (c) wherein the particulate superabsorbent polymer composition comprises i) a monomer selected from an ethylenically unsaturated carboxylic acid, ethylenically unsaturated carboxylic acid anhydride, salts or derivatives thereof, and ii) an internal crosslinker composition that is the reaction product selected from
  (α) saturated amines and/or saturated polyamines with ethylenically unsaturated glycidyl and/or ethylenically unsaturated polyglycidyl compounds,
  (β) ethylenically unsaturated amines and/or ethylenically unsaturated polyamines with saturated glycidyl and/or saturated polyglycidyl compounds, or
  (γ) ethylenically unsaturated amines and/or ethylenically unsaturated polyamines with ethylenically unsaturated glycidyl and/or ethylenically unsaturated polyglycidyl compounds;

iii) from 0.001 to 5.0 wt % based on the dry superabsorbent polymer composition powder weight of surface crosslinking agent applied to the particle surface;

wherein the particulate superabsorbent polymer composition has a Centrifuge Retention Capacity of from 20 g/g to 40 g/g as determined by the Centrifuge Retention Capacity Test set forth herein, and a gel bed permeability of at least 5 Darcy or more as determined by the Gel Bed Permeability Test set forth herein.

Numerous other aspects of embodiments, features, and advantages of the present invention will appear from the following detailed description, accompanying drawings, and claims. In the interest of brevity and conciseness, any ranges of values set forth in this specification contemplate all values within the range and are to be construed as support for claims reciting any sub-ranges having endpoints which are real number values within the specified range in question. These and other aspects, advantages, and salient features of the present invention will become apparent from the following detailed description, the accompanying drawings, and the appended claims.

BRIEF DESCRIPTION OF THE FIGURES

The foregoing and other features, aspects, and advantages of the present invention will become better understood with regard to the following description, appended claims, and accompanying drawings where:

DEFINITIONS

Figure 1:
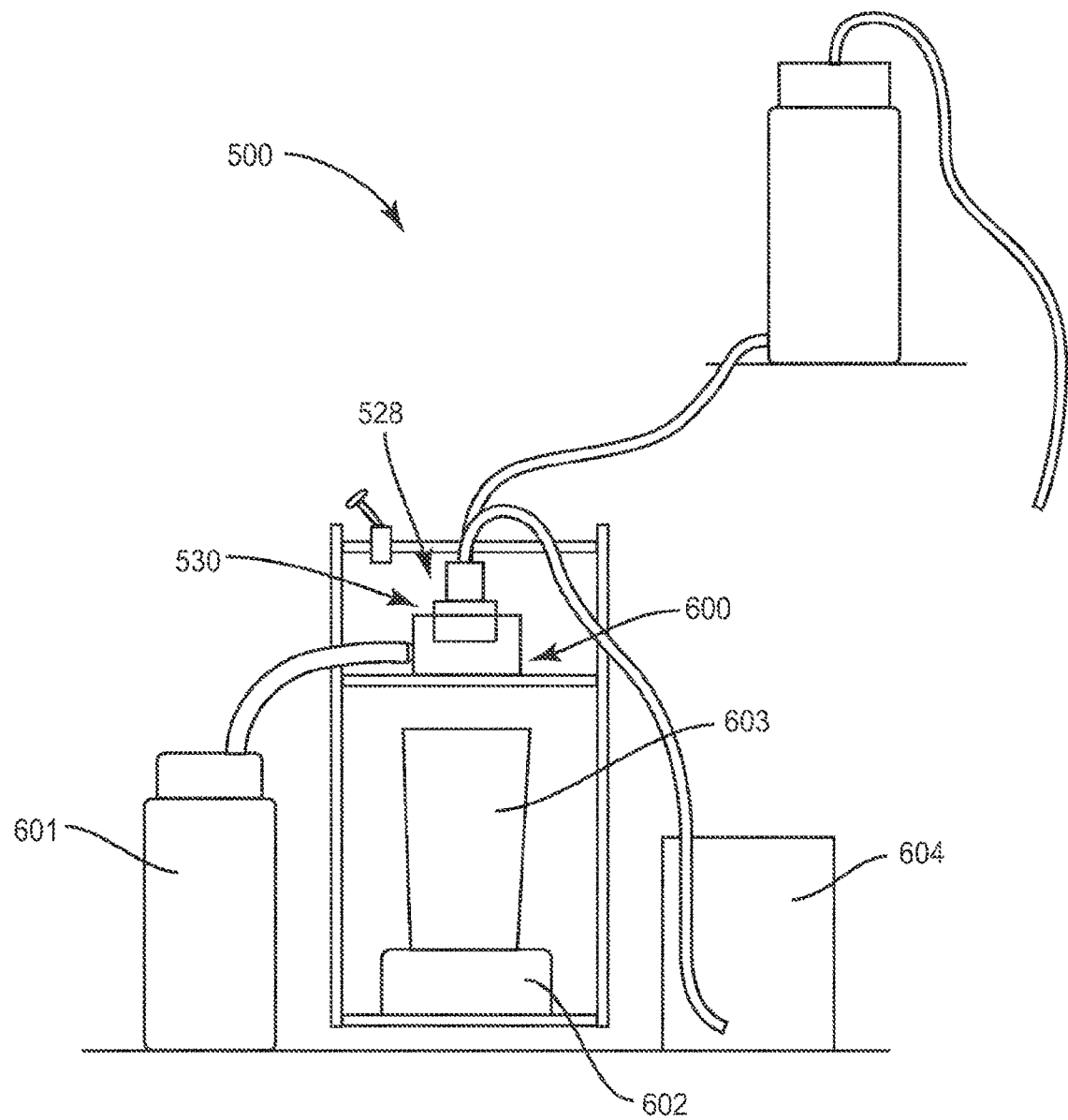
FIG. 1 is a side view of the test apparatus employed for the Free Swell Gel Bed Permeability Test.

It should be noted that, when employed in the present disclosure, the terms "comprises," "comprising," and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

As used herein, the term "about" modifying the quantity of an ingredient in the compositions of the invention or employed in the methods of the invention refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term also encompasses amounts that differ due to different equilibrium conditions for a composition resulting from a particular initial mixture. Whether or not modified by the term "about" the claims include equivalents to the quantities.

The term "absorbent article" as used herein refers to devices that absorb and contain body fluids or body exudates, and, more specifically, refers to devices that are placed against or in proximity to the body of the wearer to absorb and contain the various fluids or exudates discharged from the body. Absorbent articles may include diapers, training pants, adult incontinence undergarments, feminine hygiene products, breast pads, care mats, bibs, wound dressing products, and the like. Absorbent articles may further include floor cleaning articles, food industry articles, and the like.

The term "Centrifuge Retention Capacity (CRC)" as used herein refers to the ability of the particulate superabsorbent polymer to retain liquid therein after being saturated and subjected to centrifugation under controlled conditions and is stated as grams of liquid retained per gram weight of the sample (g/g) as measured by the Centrifuge Retention Capacity Test set forth herein.

The terms "crosslinked", "crosslink", "crosslinker", or "crosslinking" as used herein refers to any means for effectively rendering normally water-soluble materials substantially water-insoluble but swellable. Such a crosslinking means can include, for example, physical entanglement, crystalline domains, covalent bonds, ionic complexes and associations, hydrophilic associations such as hydrogen bonding, hydrophobic associations, or Van der Waals forces.

The term "internal crosslinker" or "monomer crosslinker" as used herein refers to use of a crosslinker in the monomer solution to form the polymer.

The term "Darcy" is a Gaussian unit system (CGS) unit of permeability. One Darcy is the permeability of a solid through which one cubic centimeter of fluid, having a viscosity of one centipoise, will flow in one second through a section one centimeter thick and one square centimeter in cross-section, if the pressure difference between the two sides of the solid is one atmosphere. It turns out that permeability has the same units as area; since there is no SI unit of permeability, square meters are used. One Darcy is equal to $0.98692 \times 10^{-12}$ m$^2$ or $0.98692 \times 10^{-8}$ cm$^2$.

The term "diaper" as used herein refers to an absorbent article generally worn by infants and incontinent persons about the lower torso so as to encircle the waist and legs of the wearer and that is specifically adapted to receive and contain urinary and fecal waste.

The term "disposable" as used herein refers to absorbent articles that are not intended to be laundered or otherwise restored or reused as an absorbent article after a single use. Examples of such disposable absorbent articles include, but are not limited to, personal care absorbent articles, health/medical absorbent articles, and household/industrial absorbent articles.

The term "dry superabsorbent polymer composition" as used herein generally refers to the superabsorbent polymer composition having less than 10% moisture.

The term "gel permeability" is a property of the mass of particles as a whole and is related to particle size distribution, particle shape, and the connectedness of the open pores between the particles, shear modulus, and surface modification of the swollen gel. In practical terms, the gel permeability of the superabsorbent polymer composition is a measure of how rapidly liquid flows through the mass of swollen particles. Low gel permeability indicates that liquid cannot flow readily through the superabsorbent polymer composition, which is generally referred to as gel blocking, and that any forced flow of liquid (such as a second application of urine during use of the diaper) must take an alternate path (e.g., diaper leakage).

The term "mass median particle size" of a given sample of particles of superabsorbent polymer composition is defined as the particle size, which divides the sample in half on a mass basis, i.e., half of the sample by weight has a particle size greater than the mass median particle size, and half of the sample by mass has a particle size less than the mass median particle size. Thus, for example, the mass median particle size of a sample of superabsorbent polymer composition particles is 2 microns if one-half of the sample by weight is measured as more than 2 microns.

The terms "particle," "particulate," and the like, when used with the term "superabsorbent polymer," refer to the form of discrete units. The units can comprise flakes, fibers, agglomerates, granules, powders, spheres, pulverized materials, or the like, as well as combinations thereof. The particles can have any desired shape: for example, cubic, rod like polyhedral, spherical or semi-spherical, rounded or semi-rounded, angular, irregular, et cetera.

The term "permeability", when used herein shall mean a measure of the effective connectedness of a porous structure, in this case, crosslinked polymers, and may be specified in terms of the void fraction, and extent of connectedness of the particulate superabsorbent polymer composition.

The term "polymer" includes, but is not limited to, homopolymers, copolymers, for example, block, graft, random, and alternating copolymers, terpolymers, etc., and blends and modifications thereof. Furthermore, unless otherwise specifically limited, the term "polymer" shall include all possible configurational isomers of the material. These configurations include, but are not limited to isotactic, syndiotactic, and atactic symmetries.

The term "polyolefin" as used herein generally includes, but is not limited to, materials such as polyethylene, polypropylene, polyisobutylene, polystyrene, ethylene vinyl acetate copolymer, and the like, the homopolymers, copolymers, terpolymers, etc., thereof, and blends and modifications thereof. The term "polyolefin" shall include all possible structures thereof, which include, but are not limited to, isotatic, synodiotactic, and random symmetries. Copolymers include atactic and block copolymers.

The term "superabsorbent polymer" as used herein refers to water-swellable, water-insoluble organic or inorganic materials including superabsorbent polymers and superabsorbent polymer compositions capable, under the most favorable conditions, of absorbing at least 10 times their weight, or at least 15 times their weight, or at least 25 times their weight in an aqueous solution containing 0.9 weight percent sodium chloride.

The term "superabsorbent polymer composition" as used herein refers to a superabsorbent polymer comprising a surface additive in accordance with the present invention.

The term "surface crosslinking" as used herein refers to the level of functional crosslinks in the vicinity of the surface of the superabsorbent polymer particle, which is generally higher than the level of functional crosslinks in the interior of the superabsorbent polymer particle. As used herein, "surface" describes the outer-facing boundaries of the particle.

The term "thermoplastic" as used herein describes a material that softens when exposed to heat and which substantially returns to a non-softened condition when cooled to room temperature.

The term "% by weight" or "% wt" as used herein and referring to components of the superabsorbent polymer composition, is to be interpreted as based on the weight of the dry superabsorbent polymer composition, unless otherwise specified herein.

These terms may be defined with additional language in the remaining portions of the specification.

DETAILED DESCRIPTION

While typical aspects of embodiment and/or embodiments have been set forth for the purpose of illustration, this Detailed Description and the accompanying drawings should not be deemed to be a limitation on the scope of the invention. Accordingly, various modifications, adaptations, and alternatives may occur to one skilled in the art without departing from the spirit and scope of the present invention. By way of a hypothetical illustrative example, a disclosure in this specification of a range of from 1 to 5 shall be considered to support claims to any of the following ranges: 1-5; 1-4; 1-3; 1-2; 2-5; 2-4; 2-3; 3-5; 3-4; and 4-5.

It is the object of the present invention to provide superabsorbent polymer, or a particulate superabsorbent polymer composition, cross-linked with at least one internal crosslinker composition, as well as a process for the production of the particulate superabsorbent polymer composition, wherein the particulate superabsorbent polymer composition are suitable for use in an absorbent article such as, diaper constructions, or other technical applications.

The particulate superabsorbent polymer composition of the present invention comprises a) a polymerizable unsaturated acid group containing monomer wherein the monomer is selected from unsaturated acid groups-containing monomers, ethylenically unsaturated carboxylic acid anhydride, salts, or derivatives thereof;

b) an internal crosslinker composition that is the reaction product selected from
   (i) saturated amines and/or saturated polyamines with ethylenically unsaturated glycidyl compounds and/or ethylenically unsaturated polyglycidyl compounds,
   (ii) ethylenically unsaturated amines and/or ethylenically unsaturated polyamines with saturated glycidyl compounds and/or saturated polyglycidyl compounds, or
   (iii) ethylenically unsaturated amines and/or ethylenically unsaturated polyamines with saturated glycidyl compounds and/or saturated polyglycidyl compounds, or
   (iii) ethylenically unsaturated amines and/or ethylenically unsaturated polyamines with ethylenically unsaturated glycidyl compounds and/or ethylenically unsaturated polyglycidyl compounds;
   wherein components a) and b) are polymerized and granulated to form particulate superabsorbent polymer having a particle surface, wherein at least 40 wt % of the particulate superabsorbent polymer has a particle size from 300 µm to 600 µm; and c) from 0.01 to 5 wt % based on the dry superabsorbent polymer composition powder weight of surface crosslinking agent applied to the particle surface;
wherein the particulate superabsorbent polymer composition has a Centrifuge Retention Capacity of from 20 g/g to 40 g/g as determined by the Centrifuge Retention Capacity Test set forth herein, and a gel bed permeability of at least 5 Darcy or more as determined by the Gel Bed Permeability Test set forth herein.

Another embodiment of the current invention is a method to make particulate superabsorbent polymer composition comprising the steps of:

a) preparing a superabsorbent polymer by the process of polymerizing of at least one monomer selected from an ethylenically unsaturated carboxylic acid, ethylenically unsaturated carboxylic acid anhydride, salts or derivatives thereof based on the superabsorbent polymer, and from 0.001% by weight to 1% by weight based on the monomer of an internal crosslinking composition that is the reaction product selected from
   (i) saturated amines and/or saturated polyamines with ethylenically unsaturated glycidyl compounds and/or ethylenically unsaturated polyglycidyl compounds,
   (ii) ethylenically unsaturated amines and/or ethylenically unsaturated polyamines with saturated glycidyl compounds and/or saturated polyglycidyl compounds, or
   (iii) ethylenically unsaturated amines and/or ethylenically unsaturated polyamines with ethylenically unsaturated glycidyl compounds and/or ethylenically unsaturated polyglycidyl compounds;

c) polymerizing the superabsorbent polymer;

d) granulating the superabsorbent polymer to form particulate superabsorbent polymer wherein at least 40 wt % of the particulate superabsorbent polymer has a particle size from 300 µm to 600 µm;
e) surface crosslinking the particulate superabsorbent polymer with from 0.001 to 5.0 wt % based on the dry superabsorbent polymer composition powder weight of surface crosslinking agent applied to the particle surface; and
f) heat treating the surface crosslinked particulate superabsorbent polymer of step e) at a temperature from 150° C. to 250° C. for 20 to 120 minutes to form surface crosslinked particulate superabsorbent polymer; and
wherein the particulate superabsorbent polymer composition has a Centrifuge Retention
Capacity of from 20 g/g to 40 g/g as determined by the Centrifuge Retention Capacity Test set forth herein, and a gel bed permeability of at least 5 Darcy or more as determined by the Gel Bed Permeability Test set forth herein.

Another embodiment of the current invention is a method to make particulate superabsorbent polymer composition comprising the steps of:
a) preparing a superabsorbent polymer by the process of polymerizing of at least one monomer selected from an ethylenically unsaturated carboxylic acid, ethylenically unsaturated carboxylic acid anhydride, salts or derivatives thereof based on the superabsorbent polymer, and from 0.001% by weight to 1% by weight of the monomer of an internal crosslinking composition that is the reaction product selected from
  (i) saturated amines and/or saturated polyamines with ethylenically unsaturated glycidyl compounds and/or ethylenically unsaturated polyglycidyl compounds,
  (ii) ethylenically unsaturated amines and/or ethylenically unsaturated polyamines with saturated glycidyl compounds and/or saturated polyglycidyl compounds, or
  (iii) ethylenically unsaturated amines and/or ethylenically unsaturated polyamines with ethylenically unsaturated glycidyl compounds and/or ethylenically unsaturated polyglycidyl compounds;
b) polymerizing the superabsorbent polymer;
c) granulating the superabsorbent polymer to form particulate superabsorbent polymer wherein at least 40 wt % of the particulate superabsorbent polymer has a particle size from 300 µm to 600 µm;
d) surface treating the surface crosslinked particulate superabsorbent polymer of step c) with from 0.01 to 5 wt % based on the dry superabsorbent polymer composition weight of an insoluble, inorganic powder and/or from 0.01 to 5 wt % based on the dry superabsorbent polymer composition powder weight of a multivalent metal salt,
e) surface crosslinking the particulate superabsorbent polymer with from 0.001 to 5.0 wt % based on the dry superabsorbent polymer composition weight of surface crosslinking agent applied to the particle surface; and
f) heat treating the surface crosslinked particulate superabsorbent polymer of step e) at a temperature from 150° C. to 250° C. for from 20 to 120 minutes to form surface crosslinked particulate superabsorbent polymer;
wherein the particulate superabsorbent polymer composition has a Centrifuge Retention Capacity of 20 g/g to 40 g/g as determined by the Centrifuge Retention Capacity Test set forth herein, and a Gel Bed Permeability of at least 5 Darcy or more as determined by the Gel Bed Permeability Test set forth herein.

Another embodiment of the current invention is an absorbent article absorbent article comprising: (a) a liquid pervious topsheet; (b) a liquid impervious backsheet; (c) a core positioned between (a) and (b), said core comprising 10% to 100% by weight of the particulate superabsorbent polymer composition and 0 wt % to 90 wt % by weight of hydrophilic fiber material; (d) optionally a tissue layer positioned directly above and below said core (c); and (e) optionally an acquisition layer positioned between (a) and (c) wherein the particulate superabsorbent polymer composition comprises
i) a monomer selected from an ethylenically unsaturated carboxylic acid, ethylenically unsaturated carboxylic acid anhydride, salts or derivatives thereof, and ii) an internal crosslinker composition that is the reaction product selected from
  (α) saturated amines and/or saturated polyamines with ethylenically unsaturated glycidyl compounds and/or ethylenically unsaturated polyglycidyl compounds,
  (β) ethylenically unsaturated amines and/or ethylenically unsaturated polyamines with saturated glycidyl compounds and/or saturated polyglycidyl compounds, or
  (γ) ethylenically unsaturated amines and/or ethylenically unsaturated polyamines with ethylenically unsaturated glycidyl compounds and/or ethylenically unsaturated polyglycidyl compounds;
iii) from 0.001 to 5.0 wt % based on the dry superabsorbent polymer composition powder weight of surface crosslinking agent applied to the particle surface;
wherein the particulate superabsorbent polymer composition has a Centrifuge Retention
Capacity of from 20 g/g to 40 g/g as determined by the Centrifuge Retention Capacity Test set forth herein, and a gel bed permeability of at least 5 Darcy or more as determined by the Gel Bed Permeability Test set forth herein.

The particulate superabsorbent polymer composition as set forth in embodiments of the present invention is obtained by the initial polymerization of from 55% to 99.9% by weight of the superabsorbent polymer of polymerizable unsaturated acid group containing monomer. A suitable polymerizable monomer includes any of those containing carboxyl groups, such as acrylic acid, methacrylic acid, or 2-acrylamido-2-methylpropanesulfonic acid, or mixtures thereof. It is desirable for at least 50% by weight, and more desirable for at least 75% by weight of the acid groups to be carboxyl groups.

As to acrylic acid, it is important to use acrylic acid that is known by its contents to be pure, that is the acrylic acid having at least 99.5 wt % concentration, or at least 99.7 wt % concentration, or at least 99.8% concentration. The principal component of this monomer may be either acrylic acid, or acrylic acid and an acrylate salt. Impurities in acrylic acid may include water, propionic acid, acetic acid, and diacrylic acid, commonly called acrylic acid dimer. Content of the diacrylic acid should be 1000 ppm or less, or 500 ppm or less, or 300 ppm or less, when the acrylic acid is used in the process. In addition, it is important to minimize the generation of β-hydroxyproprionic acid during the neutralization process to less than 1000 ppm, or less than 500 ppm, of β-hydroxyproprionic acid.

Moreover, in the acrylic acid, the content of protoanemonin and/or furfural is 0 to 20 ppm by weight in terms of the converted value based on acrylic acid. In light of improvement physical properties and characteristics of the water absorbing resin, content of protoanemonin and/or furfural in the monomer is not higher than 10 ppm by weight, or from 0.01 to 5 ppm by weight, or from 0.05 to 2 ppm by weight, or from 0.1 to 1 ppm by weight in terms of the converted value based on acrylic acid.

Further, in the monomer, it is preferred that the amount of aldehyde component other than furfural and/or maleic acid is as small as possible for the same reason. Specifically, the content of the aldehyde component other than furfural and/or maleic acid may be from 0 to 5 ppm by weight, or from 0 to 3 ppm by weight, or from 0 to 1 ppm by weight, or 0 ppm by weight (not higher than detection limit) in terms of the converted value based on acrylic acid. Examples of the aldehyde component other than furfural include benzaldehyde, acrolein, acetaldehyde and the like.

Additionally, in the monomer or particulate water absorbing agent of the present invention, content of saturated carboxylic acid consisting of acetic acid and/or propionic acid, not higher than 1000 ppm by weight, or from 10 to 800 ppm by weight, or from 100 to 500 ppm by weight in terms of the converted value based on acrylic acid.

In some aspects, the suitable monomer that can be copolymerized with the ethylenically unsaturated monomer may include, but is not limited to acrylamide, methacrylamide, hydroxyethyl acrylate, dimethylaminoalkyl (meth)-acrylate, ethoxylated (meth)-acrylates, dimethylaminopropylacrylamide, or acrylamidopropyltrimethylammonium chloride. Such monomer may be present in a range of from 0% to 40 wt % of the copolymerized monomer.

The acid groups may be neutralized to the extent of at least 25 mol %, that is, the acid groups are desirably present as sodium, potassium, or ammonium salts. The neutralization may be accomplished by either adding a caustic solution to a monomer solution, or by adding the monomer solution to a caustic solution. In some aspects, the degree of neutralization may be at least 50 mol % or may be from 50 mol % to 80 mol %. It may be desirable to utilize polymers obtained by polymerization of acrylic acid or methacrylic acid, the carboxyl groups of which are neutralized to the extent of from 50 mol % to 80 mol %, in the presence of internal crosslinking agents.

When partially neutralized, or completely neutralized, acrylate salt is turned into the polymer, the converted value based on acrylic acid may be determined through converting the partially neutralized or completely neutralized polyacrylate salt is assumed to be entirely the equimolar unneutralized polyacrylic acid.

The superabsorbent polymer includes crosslinking points wherein the superabsorbent polymer can be crosslinked with an internal crosslinking composition. Suitable internal crosslinker compositions in this embodiment may include, but are not limited to an internal crosslinker composition which is the reaction product selected from
(i) saturated amines and/or saturated polyamines with ethylenically unsaturated glycidyl compounds and/or ethylenically unsaturated polyglycidyl compounds,
(ii) ethylenically unsaturated amines and/or ethylenically unsaturated polyamines with saturated glycidyl compounds and/or saturated polyglycidyl compounds, or
(iii) ethylenically unsaturated amines and/or ethylenically unsaturated polyamines with ethylenically unsaturated glycidyl compounds and/or ethylenically unsaturated polyglycidyl compounds.

The saturated amines, ethylenically unsaturated amines, saturated polyamines, and/or ethylenically unsaturated polyamines may include aliphatic as well as aromatic, heterocyclic and cyclic compounds as suitable amines components for the reaction with the glycidyl compounds; including for example, (mono, di and poly)aminoalkanes, (mono, di and poly)aminopolyethers, allylamine, alkyl(meth)allylamines, e.g., methyl allylamine, methyl methallylamine, ethyl methallylamine, and ethyl allylamine; methyl-, ethyl-, propyl- and butylamine, diallylamine (DAA), dimethallylamine, aniline, ethylene diamine (EDA), diethylene triamine, hexamethylenediamine, trimethylhexamethylene diamine, neopentane diamine, 1,2-propylene diamine, 4,7-dioxadecane-1,10-diamine, 4,9-dioxadodecane-1,12-diamine, polyether diamines, polyalkylene glycol diamines, 3-amino-1-methylaminopropane, bis(3-aminopropyl)methylamine, isophorone diamine, 4,4'-diaminodicyclohexylmethane, 1-(2-aminoethyl)piperazine, o-, m-, or p-phenylene diamine, 4',4'-diaminodiphenylmethane, 1,4-diaminoanthraquinone, 2,4,6-triamino-1,3,5-triazine, aminopyridine, glucosamine, and mixtures thereof.

The ethylenically unsaturated glycidyl compounds, ethylenically unsaturated polyglycidyl compounds, saturated glycidyl compounds, and/or saturated polyglycidyl compounds to be used according to the present invention may be mono-, di- or polyfunctional. Examples of monofunctional compounds used alone or in admixture include: ethylene glycol monoglycidyl ether and the related $C_1$-$C_6$-alkyl ethers or esters; glycidol, ethylene oxide (EO), propylene oxide (PO), (meth)allyl glycidyl ethers (AGE), (meth)allyl glycidyl ethers, polyethylene glycol monoglycidyl ethers and the related $C_1$-$C_6$-alkyl ethers or esters; vinyl glycidyl ethers, glycidyl(meth)acrylates, glycidyl(meth)allyl ethers, or 1-halogen-2,3-epoxypropane. Ethylene glycol or polyglycol diglycidyl ethers; glycerol, trimethylolpropane, or pentaerythritol triglycidyl ethers; polyglycerol polyglycidyl ethers, sorbitol polyglycidyl ethers, or their mixtures are used as multifunctional glycidyl ethers. The above-mentioned polyethylene glycol chains of the glycidyl compounds may comprise up to 45, or up to 20, or up to 12 ethylene glycol units.

The following structures as shown in Table 1 are examples for suitable glycidyl compounds.

TABLE 1

| Name | Structure |
|---|---|
| allyl glycidyl ether (AGE) | 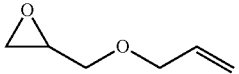 |
| glycidyl methacrylate | 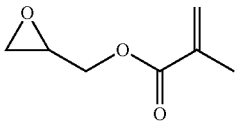 |
| glycidyl acrylate | 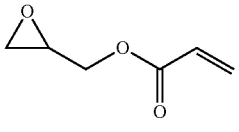 |
| EGDGE (ethylene glycol dicglycidylether) | 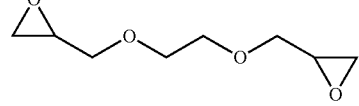 |

In another embodiment of the present invention, the internal crosslinking agents may be alkoxylated at the site of the free hydroxyl or NH groups. To this end, the alcohols according to the present invention are reacted, for example, with ethylene or propylene oxide or their mixtures. The reaction with ethylene oxide, EO, can also achieve improved water solubility of the cross-linker. Up to 45 moles EO, or up to 20 moles EO, or up to 12 moles EO may be added per hydroxyl group. Propylene oxide may be used in place of EO.

Some examples of internal crosslinking agents according to the present invention include, but are not limited to, diallylaminoethanol, diallylaminopolyglycol ether, 1,3-bis(diallylamino)-2-propanol, N,N-diallylamino-1-amino-3-allyloxy-2-propanol, polyethylene glycol di(N,N-diallyl-3-amino-2-hydroxy-prop-1-yl)ether, ethylene glycol di(N,N-diallyl-3-amino-2-hydroxy-prop-1-yl)ether, alkoxylated 1,3-bis(diallylamino)-2-propanol, alkoxylated 1-allyloxy-3-(diallylamino)-2-propanol, alkoxylated polyethylene glycol di(N,N-diallyl-3-amino-2-hydroxy-prop-1-yl)ether, alkoxylated ethylene glycol di(N,N-diallyl-3-amino-2-hydroxy-prop-1-yl)ether, N,N-di(allyloxy-2-hydroxy-prop-3-yl)aniline, alkoxylated N,N-di(allyloxy-2-hydroxy-prop-3-yl)aniline, 1,2-bis[N,N-di(allyloxy-2-hydroxy-prop-3-yl)]ethane and bis[N,N-di(allyloxy-2-hydroxy-prop-3-yl)]aminoethyl-(allyloxy-2-hydroxy-prop-3-yl)amine plus alkoxylated products thereof. The above-mentioned polyethylene glycol ether units may comprise a maximum of 45 moles of ethylene oxide and/or propylene oxide, or a maximum of 20, or a maximum of 15 moles of ethylene oxide and/or propylene oxide. According to another embodiment of the present invention, the N-atoms of the cross-linkers are partially or completely quaternized.

The internal crosslinking agents or their mixtures to be used according to the present invention are used in amounts of from 0.01 to 3.0%-wt %, or from 0.02 to 1.5%-wt %, or from 0.03 to 1.0%-wt %, relative to the polymerizable unsaturated acid group containing monomer.

In another embodiment, the superabsorbent polymer may include from 0.001 to 0.5 wt % based on the polymerizable unsaturated acid group containing monomer of a second, different internal crosslinker selected from compositions comprising at least two ethylenically unsaturated double-bonds, for example, methylenebisacrylamide or -methacrylamide or ethylenebisacrylamide; esters of unsaturated mono- or polycarboxylic acids of polyols, such as, diacrylates or triacrylates, e.g., butanediol- or ethylene glycol diacrylate or -methacrylate; trimethylolpropane triacrylate, as well as their alkoxylated derviatives; additionally, allyl compounds, such as allyl (meth)acrylate, triallyl cyanurate, maleic acid diallyl ester, polyallyl ester, tetraallyloxyethane, di- and triallylamine, tetrallylethylenediamine, allyl esters of phosphoric acid or phosphorous acid. Moreover, compounds having at least one functional group reactive towards acid groups may also be used. Examples thereof include tetrakis-N,N,N',N',[3-allyloxy-2-hydroxy propyl]diethylene diamine, N-methylol compounds of amides, such as methacrylamide or acrylamide, and the ethers derived therefrom, as well as di- and polyglycidyl compounds.

In some aspects, initiators can be added to the monomer solution for initiation of the free-radical polymerization. Suitable initiators include, but are not limited to, azo or peroxo compounds, redox systems or ultraviolet initiators, sensitizers, and/or radiation.

After polymerization, the superabsorbent polymer, existing in gel form, is generally formed, or granulated, into superabsorbent polymer particles, or particulate superabsorbent polymer. The particulate superabsorbent polymer of the present invention generally includes particle sizes ranging from 50 to 1000 µm, or from 150 to 850 µm. The present invention may include at least 40 wt % of the particles having a particle size from 300 µm to 600 µm, at least 50 wt % of the particles having a particle size from 300 µm to 600 µm, or at least 60 wt % of the particles having a particle size from 300 µm to 600 µm as measured by screening through a U.S. standard 30 mesh screen and retained on a U.S. standard 50 mesh screen. In addition, the size distribution of the superabsorbent polymer particles of the present invention may include less than 30% by weight of particles having a size greater than 600 µm, and less than 30% by weight of particles having a size of less than 300 µm as measured using for example a RO-TAP® Mechanical Sieve Shaker Model B available from W. S. Tyler, Inc., Mentor Ohio.

The particulate superabsorbent polymer may then be surface treated with additional chemicals and treatments as set forth herein. In particular, the surface of the particulate superabsorbent polymer may be crosslinked, generally referred to as surface crosslinking, by the addition of a surface crosslinking agent and heat-treatment. In general, surface crosslinking is a process that is believed to increase the crosslink density of the polymer matrix in the vicinity of the particulate superabsorbent polymer surface with respect to the crosslinking density of the particle interior. It is noted that treatment of the particulate superabsorbent polymer with inorganic particles and/or water or aqueous solutions can be performed either before or after surface crosslinking.

Desirable surface crosslinking agents may include chemicals with one or more functional groups that are reactive toward pendant groups of the polymer chains, typically the acid groups. Surface crosslinker agents may include compounds that comprise at least two functional groups which can react with functional groups of a polymer structure in a condensation reaction, (condensation crosslinker), in an addition reaction or in a ring opening reaction. These compounds may include condensation crosslinkers such as, for example, diethylene glycol, triethylene glycol, polyethylene glycol, glycerine, polyglycerine, propylene glycol, diethanolamine, triethanolamine, polyoxypropylene, oxyethylene-oxypropylene block copolymers, sorbitan fatty acid esters, polyoxyethylene sorbitan fatty acid esters, trimethylolpropane, pentaerythritol, polyvinyl alcohol, sorbitol, 1,3-dioxolan-2-one (ethylene carbonate), 4-methyl-1,3-dioxolan-2-one (propylene carbonate), 4,5-dimethyl-1,3-dioxolan-2-one, 4,4-dimethyl-1,3-dioxolan-2-one, 4-ethyl-1,3-dioxolan-2-one, 4-hydroxymethyl-1,3-dioxolan-2-one, 1,3-dioxan-2-one, 4-methyl-1,3-dioxan-2-one, 4,6-dimethyl-1,3-dioxan-2-one as well as 1,3-dioxolan-2-one. The amount of the surface crosslinking agent may be present in an amount of from 0.01% to 5% by weight of the dry superabsorbent polymer composition, and such as from 0.1% to 3% by weight, and such as from 0.1 wt % to 1 wt %, based on the weight of the dry particulate superabsorbent polymer.

After the particulate superabsorbent polymer have been brought into contact with the surface crosslinker composition, or with the fluid comprising the surface crosslinker composition, the treated particulate superabsorbent polymer is heat treated which may include heating the treated particulate superabsorbent polymer to a temperature of from 50° C. to 300° C., or from 75° C. to 275° C., or from 150° C. to 250° C., so that the outer region of the polymer structures is more strongly crosslinked compared to the inner region (i.e., surface crosslinking). The duration of the heat treatment is limited by the risk that the desired property profile of the polymer structures will be destroyed as a result of the effect of heat.

In another embodiment, the fluid comprising the surface crosslinker, may further include other ingredients, separately or together, including multivalent metal cations such as aluminum sulfate or aluminum lactate, and/or an insoluble, inorganic powder such as a silica including SIPERNAT® 22S fumed silica available from Evonik Industries, which ingredients will be hereafter described in more detail.

In one aspect of surface crosslinking, the particulate superabsorbent polymer is coated or surface-treated, with an alkylene carbonate, such as ethylene carbonate, followed by heating to affect surface crosslinking, which can improve the surface crosslinking density and the gel strength characteristics of the superabsorbent polymer particle. More specifically, the surface crosslinking agent is coated onto the superabsorbent polymer particulate by mixing the particulate superabsorbent polymer with an aqueous alcoholic solution of the alkylene carbonate surface crosslinking agent. The amount of alcohol in the aqueous alcoholic solution may be determined by the solubility of the alkylene carbonate and is kept as low as possible for various reasons, for instance, for protection against explosions. Suitable alcohols are methanol, isopropanol, ethanol, butanol, or butyl glycol, as well as mixtures of these alcohols. In some aspects, the solvent desirably is water, which typically is used in an amount of 0.3% by weight to 5.0% by weight, based on the weight of the dry superabsorbent polymer composition.

In other aspects, the alkylene carbonate surface crosslinking agent is dissolved in water without any alcohol. In still other aspects, the alkylene carbonate surface crosslinking agent may be applied from a powder mixture, for example, with an inorganic carrier material, such as silicone dioxide ($SiO_2$), or in a vapor state by sublimation of the alkylene carbonate.

To achieve the desired surface crosslinking properties, the alkylene carbonate should be distributed evenly on the particulate superabsorbent polymer. For this purpose, mixing is effected in suitable mixers known in the art, such as fluidized bed mixers, paddle mixers, rotary drum mixers, or twin-worm mixers. It is also possible to carry out the coating of the particulate superabsorbent polymer during one of the process steps in the production of the particulate superabsorbent polymer.

The heat treatment, which follows the coating treatment of the particulate superabsorbent polymer with a solution of surface crosslinking agent, may be carried out as follows. In general, the heat treatment is done at a temperature of from 100° C. to 300° C. Lower temperatures are possible if highly reactive epoxide crosslinking agents are used. However, if alkylene carbonates are used, then the thermal treatment is suitably at a temperature of from 150° C. to 250° C. In this particular aspect, the treatment temperature depends on the dwell time and the kind of alkylene carbonate. For example, at a temperature of 150° C., the thermal treatment is carried out for one hour or longer. In contrast, at a temperature of 250° C., a few minutes (e.g., from 0.5 minutes to 5 minutes) are sufficient to achieve the desired surface crosslinking properties. The thermal treatment may be carried out in conventional dryers, or ovens, known in the art.

In addition to surface crosslinking including the heat treatment step, the particulate superabsorbent polymer compositions of the present invention may be further surface treated with other chemical compositions for the purpose of affecting of improving properties such as strength, permeability, processability, odor control, color, etc. These additives may be applied to the particulate superabsorbent polymer composition before, during or after the surface crosslinking wherein the additives may be applied before the surface crosslinking agent, or with the surface crosslinking agent, or after the surface crosslinking agent and before heat treatment, or after the heat treatment.

The particulate superabsorbent polymer composition according to the invention may include from 0 to 5 wt %, based on the dry superabsorbent polymer composition weight, of a penetration modifier that is added immediately before, during or immediately after the surface crosslinking. Examples of penetration modifiers include compounds which alter the penetration depth of surface-modifying agents into the superabsorbent polymer particle, fiber, film, foam or bead by changing the viscosity, surface tension, ionic character or adhesion of said agents or medium in which these agents are applied. Penetration modifiers may include polyethylene glycols, tetraethylene glycol dimethyl ether, monovalent metal salts, surfactants and water soluble polymers.

The particulate superabsorbent polymer composition according to the invention may comprise include from 0.01 wt % to 5 wt %, or from 0.01 wt % to 1wt %, or from 0.01 wt % to 0.5 wt % based on the dry superabsorbent polymer composition weight of a multivalent metal salt, based on the weight of the mixture, on the surface of the particulate superabsorbent polymer. The multivalent metal salt is preferably water soluble. Examples of metal cations include the cations of Al, Fe, Zr, Mg, Ce, and Zn. Preferably, the multivalent metal salt has a valence of at least +3, with Al being most preferred. Examples of anions in the multivalent metal salt include halides, sulfates, nitrates, lactates, and acetates, with chlorides, sulfates, and acetates being preferred, sulfates and lactates being more preferred. Aluminum sulfate and aluminum lactate are examples of multivalent metal salt, and are readily commercially available. The preferred form of aluminum sulfate is hydrated aluminum sulfate, preferably aluminum sulfate having from 12 to 14 waters of hydration. Mixtures of multivalent metal salts may be employed.

The superabsorbent polymer and multivalent metal salt suitably are mixed by dry blending, or in solution, using means well known to those skilled in the art. With dry blending, a binder may be employed in an amount which is sufficient to ensure that a substantially uniform mixture of the salt and the superabsorbent polymer is maintained. The binder may be water or a low volatile organic compound having a boiling point of at least 150° C. Examples of binders include water, polyols such as propylene glycol, glycerin and poly(ethylene glycol).

The particulate superabsorbent polymer composition according to the invention can comprise from 0.01 wt % to 5 wt %, or from 0.01 wt % to 1 wt %, or from 0.01 wt % to 0.5 wt % based on dry superabsorbent polymer composition powder weight of a water-insoluble, inorganic powder. Examples of insoluble, inorganic powders include silicon dioxide, silicic acid, silicates, titanium dioxide, aluminum oxide, magnesium oxide, zinc oxide, talc, calcium phosphate, clays, diatomataceous earth, zeolites, bentonite, kaolin, hydrotalcite, activated clays, etc. The insoluble inorganic powder additive may be a single compound or a mixture of compounds selected from the above list. Of all these examples, amorphous silicon dioxide or aluminum oxide. An example of silica is SIPERNAT® 22S fumed silica commercially available from Evonik Industries. Further, a particle diameter of the inorganic powder may be 1,000 μm or smaller, or 100 μm or smaller.

In some aspects, the particulate superabsorbent polymer composition of the present invention may be surface treated with from 0 wt % to 5 wt %, or from 0.001 wt % to 1 wt %, or from 0.01 wt % to 0.5 wt % of the dry superabsorbent polymer composition powder weight of a polymeric coating, such as a thermoplastic coating, or a cationic coating, or a combination of a thermoplastic coating and a cationic coating. In some particular aspects, the polymeric coating desirably is a polymer that may be in a solid, emulsion, suspension, colloidal, or solubilized state, or combinations thereof. Polymeric coatings suitable for this invention may include, but are not limited to, a thermoplastic coating having a thermoplastic melt temperature wherein the polymeric coating is applied to the particle surface coincident with or followed by a temperature of the treated superabsorbent polymer particle at the thermoplastic melt temperature.

Examples of thermoplastic polymers include polyolefin, polyethylene, polyester, polyamide, polyurethane, styrene polybutadiene, linear low density polyethylene (LLDPE), ethylene acrylic acid copolymer (EAA), ethylene alkyl methacrylate copolymer (EMA), polypropylene (PP), maleated polypropylene, ethylene vinyl acetate copolymer (EVA), polyester, polyamide, and blends of all families of polyolefins, such as blends of PP, EVA, EMA, EEA, EBA, HDPE, MDPE, LDPE, LLDPE, and/or VLDPE, may also be advantageously employed. The term polyolefin as used herein is defined above. In particular aspects, maleated polypropylene is a preferred thermoplastic polymer for use in the present invention. A thermoplastic polymer may be functionalized to have additional benefits such as water solubility or dispersability.

A cationic polymer as used herein refers to a polymer or mixture of polymers comprising a functional group or groups having a potential of becoming positively charged ions upon ionization in an aqueous solution. Suitable functional groups for a cationic polymer include, but are not limited to, primary, secondary, or tertiary amino groups, imino groups, imido groups, amido groups, and quaternary ammonium groups. Examples of synthetic cationic polymers include the salts or partial salts of poly(vinyl amines), poly(allylamines), poly(ethylene imine), poly(amino propanol vinyl ethers), poly(acrylamidopropyl trimethyl ammonium chloride), poly(diallyldimethyl ammonium chloride). Examples of natural-based cationic polymers include partially deacetylated chitin, chitosan, and chitosan salts. Synthetic polypeptides such as polyasparagins, polylysines, polyglutamines, and polyarginines are also suitable cationic polymers.

In some aspects, additional surface additives may optionally be employed with the particulate superabsorbent polymer compositions, including odor-binding substances, such as cyclodextrins, zeolites, inorganic or organic salts, and similar materials; anti-caking additives, flow modification agents, surfactants, viscosity modifiers, and the like. In addition, surface additives may be employed that perform several roles during surface modifications. For example, a single additive may be a surfactant, viscosity modifier, and may react to crosslink polymer chains.

In some aspects, the particulate superabsorbent polymer compositions of the present invention may be, after a heat treatment step, treated with water so that the superabsorbent polymer composition has a water content of up to 10% by weight, or from 1 to 6% by weight, of the superabsorbent polymer composition weight. This water may be added, with one or more of the surface additives from above, to the superabsorbent polymer.

The superabsorbent polymer according to the invention may be desirably prepared by two methods. The composition can be prepared continuously or discontinuously in a large-scale industrial manner, the after-crosslinking according to the invention being carried out accordingly.

According to one method, the partially neutralized monomer, such as acrylic acid, is converted into a gel by free-radical polymerization in aqueous solution in the presence of crosslinking agents and any further components, and the gel is comminuted, dried, ground, and sieved off to the desired particle size. This polymerization can be carried out continuously or discontinuously. For the present invention, the size of the high-capacity particulate superabsorbent polymer composition is dependent on manufacturing processes including milling and sieving. It is well known to those skilled in the art that particle size distribution of the superabsorbent polymer particles resembles a normal distribution or a bell shaped curve. It is also known that for various reasons, the normal distribution of the particle size distribution may be skewed in either direction.

According to another method, inverse suspension and emulsion polymerization can also be used for preparation of the products according to the invention. According to these processes, an aqueous, partly neutralized solution of monomer, such as acrylic acid, is dispersed in a hydrophobic, organic solvent with the aid of protective colloids and/or emulsifiers, and the polymerization is started by free radical initiators. The internal crosslinking agents may be either dissolved in the monomer solution and are metered in together with this, or are added separately and optionally during the polymerization. The addition of a water-soluble polymer as the graft base, optionally, takes place via the monomer solution or by direct introduction into the oily phase. The water is then removed azeotropically from the mixture, and the polymer is filtered off and optionally dried. Internal crosslinking can be carried out by polymerizing in a polyfunctional crosslinking agent dissolved in the monomer solution and/or by reaction of suitable crosslinking agents with functional groups of the polymer during the polymerization steps.

The result of these methods is a superabsorbent polymer or a superabsorbent polymer preproduct. A superabsorbent polymer preproduct as used herein is produced by repeating all of the steps for making the superabsorbent, up to and including drying the material, and coarse grinding in a crusher, and removing particles greater than 850 microns and smaller than 150 microns.

The particulate superabsorbent polymer composition of the present invention exhibits certain characteristics, or properties, as measured by Centrifuge Retention Capacity, Absorbency Under Load at 0.9 psi (AUL (0.9 psi)), Gel Bed Permeability (GBP), Absorbency at Pressure at 0.7 psi (AAP (0.7 psi)), and Saline Flow Conductivity (SFC).

The resultant CRC is stated as grams of liquid retained per gram weight of the sample (g/g) and may be from 20 g/g to 40 g/g, from 22 g/g to 35 g/g, or from 24 g/g to 30 g/g.

The Absorbency Under Load at 0.9 psi (AUL (0.9 psi)) may range from 12 g/g to 30 g/g, or from 15 g/g to 25 g/g.

The Gel Bed Permeability (GBP) may be at least 5 Darcy or more, or from 10 Darcy to 200 Darcy, or from 20 Darcy to 150 Darcy.

The Absorption at Pressure at 0.7 psi (AAP (0.7 psi)) may range from 20 g/g to 30 g/g.

The permeability as measured by the Saline Flow Conductivity (SFC) test may range from $20 \times 10^{-7} * cm^3 * s * g^{-1}$ to $200 \times 10^{-7} * cm^3 * s \cdot g^{-1}$.

The superabsorbent polymer compositions according to the present invention can be employed in many absorbent articles including sanitary towels, diapers, or wound coverings, and they have the property that they rapidly absorb large amounts of menstrual blood, urine, or other body fluids. Since the agents according to the invention retain the absorbed liquids even under pressure and are also capable of distributing further liquid within the construction in the swollen state, they are more desirably employed in higher concentrations, with respect to the hydrophilic fiber material, such as fluff, when compared to conventional current superabsorbent compositions. They are also suitable for use as a homogeneous superabsorber layer without fluff content within the diaper construction, as a result of which particularly thin articles are possible. The polymers are furthermore suitable for use in hygiene articles (incontinence products) for adults.

Absorbent articles, like diapers, may include (a) a liquid pervious topsheet; (b) a liquid impervious backsheet; (c) a core positioned between (a) and (b) and comprising 10% to 100%, or from 50% to 100%, by weight of the present polyamine-coated SAP particles, and 0% to 90% by weight of hydrophilic fiber material; (d) optionally a tissue layer positioned directly above and below said core (c); and (e) optionally an acquisition layer positioned between (a) and (c).

Test Procedures

Centrifuge Retention Capacity Test (CRC).

The CRC Test measures the ability of the superabsorbent polymer to retain liquid therein after being saturated and subjected to centrifugation under controlled conditions. The resultant retention capacity is stated as grams of liquid retained per gram weight of the sample, (g/g).

The retention capacity is measured by placing 0.16 grams of the pre-screened superabsorbent polymer sample into a water-permeable bag that will contain the sample while allowing a test solution (0.9 weight percent sodium chloride in distilled water) to be freely absorbed by the sample. A heat-sealable tea bag material, such as that available from Dexter Corporation (having a place of business in Windsor Locks, Conn., U.S.A.) as model designation 1234T heat sealable filter paper works well for most applications. The bag is formed by folding a 5-inch by 3-inch sample of the bag material in half and heat-sealing two of the open edges to form a 2.5-inch by 3-inch rectangular pouch. The heat seals are 0.25 inches inside the edge of the material. After the sample is placed in the pouch, the remaining open edge of the pouch is also heat-sealed. Empty bags are also made to serve as controls. Three samples are prepared for each superabsorbent polymer composition to be tested.

The sealed bags are submerged in a pan containing the test solution at an assigned testing temperature, making sure that the bags are held down until they are completely wetted. After wetting, the samples remain in the solution for an assigned period of testing time, at which time they are removed from the solution and temporarily laid on a non-absorbent flat surface.

The wet bags are then placed into the basket wherein the wet bags are separated from each other and are placed at the outer circumferential edge of the basket, wherein the basket is of a suitable centrifuge capable of subjecting the samples to a g-force of 350. One suitable centrifuge is a CLAY ADAMS DYNAC II, model #0103, having a water collection basket, a digital rpm gauge, and a machined drainage basket adapted to hold and drain the flat bag samples. Where multiple samples are centrifuged, the samples are placed in opposing positions within the centrifuge to balance the basket when spinning. The bags (including the wet, empty bags) are centrifuged at 1,600 rpm (e.g., to achieve a target g-force of 350 g force with a variance from 240 to 360 g force), for 3 minutes. G force is defined as an unit of inertial force on a body that is subjected to rapid acceleration or gravity, equal to 32 ft/sec$^2$ at sea level. The bags are removed and weighed, with the empty bags (controls) being weighed first, followed by the bags containing the superabsorbent polymer composition samples. The amount of solution retained by the superabsorbent polymer sample, taking into account the solution retained by the bag itself, is the centrifuge retention capacity (CRC) of the superabsorbent polymer, expressed as grams of fluid per gram of superabsorbent polymer. More particularly, the retention capacity is determined by the following equation:

$$CRC=[\text{sample bag after centrifuge}-\text{empty bag after centrifuge}-\text{dry sample weight}]/\text{dry sample weight}$$

The three samples are tested, and the results are averaged to determine the CRC of the superabsorbent polymer composition.

Free-Swell Gel Bed Permeability Test (FSGBP)

Figure 2:
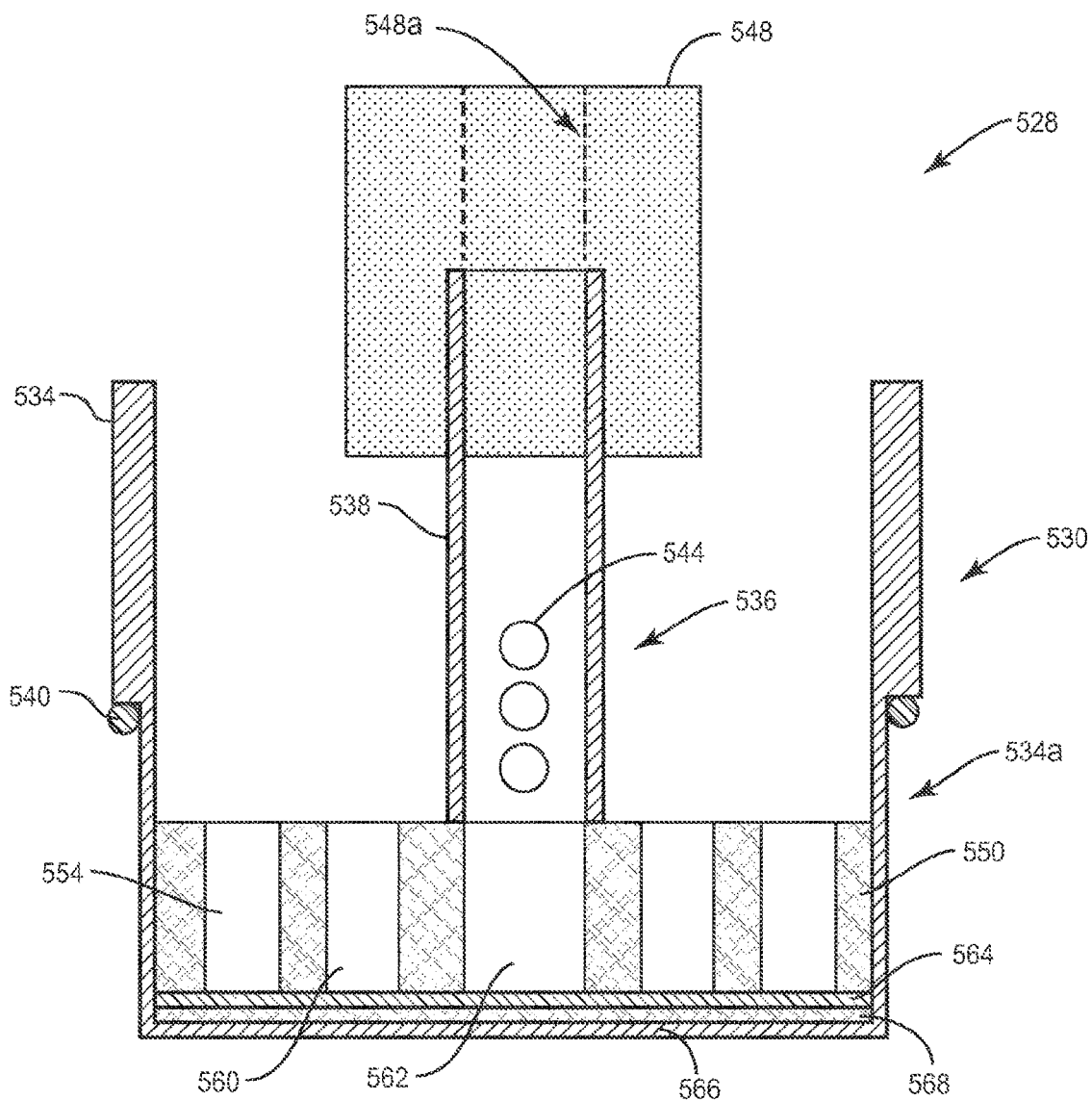
FIG. 2 is a cross-sectional side view of a cylinder/cup assembly employed in the Free Swell Gel Bed Permeability Test apparatus shown in FIG. 1.
Figure 3:
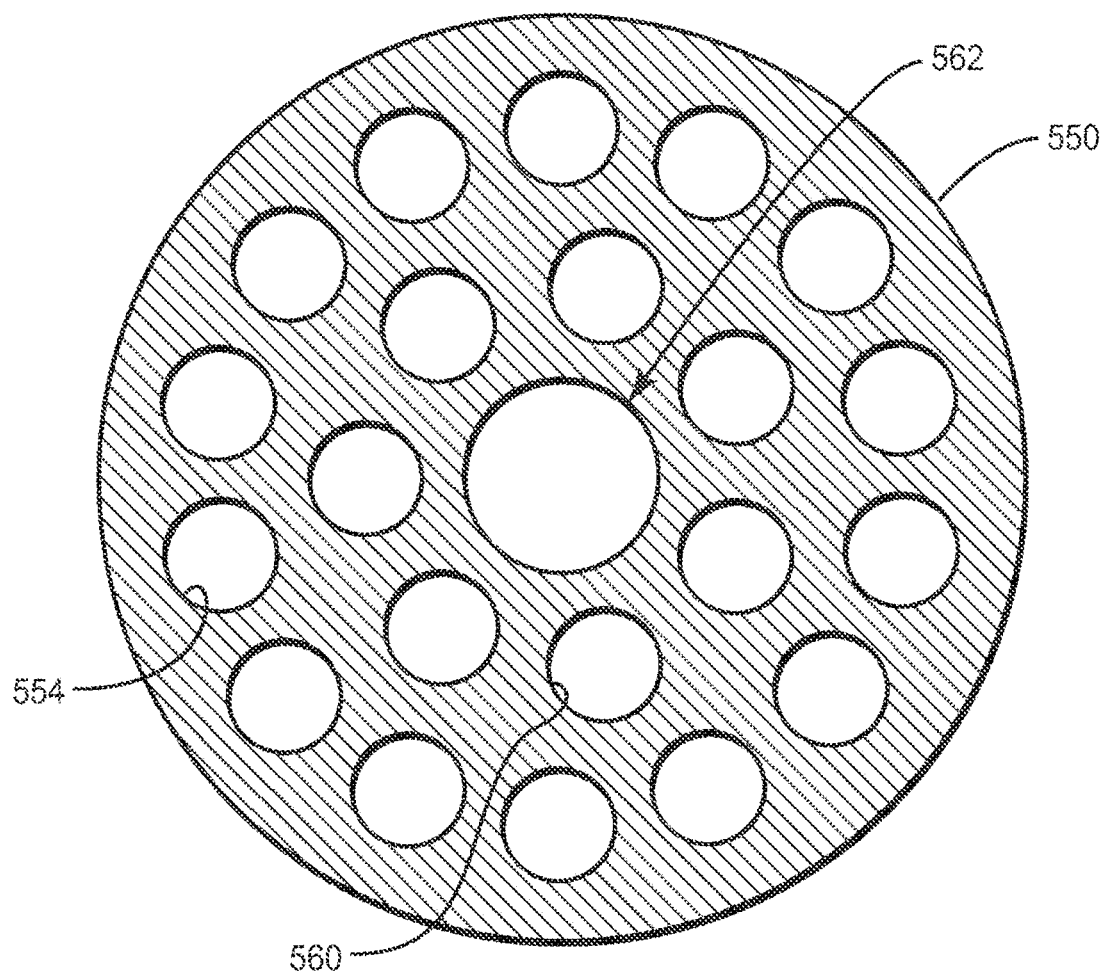
FIG. 3 is a top view of a plunger employed in the Free Swell Gel Bed Permeability Test apparatus shown in FIG. 1.

As used herein, the Free-Swell Gel Bed Permeability Test, also referred to as the Gel Bed Permeability (GBP) Under 0 psi Swell Pressure Test, determines the permeability of a swollen bed of gel particles (e.g., such as the surface treated absorbent material or the superabsorbent material prior to being surface treated), under what is commonly referred to as "free swell" conditions. The term "free swell" means that the gel particles are allowed to swell without a restraining load upon absorbing test solution as will be described. A suitable apparatus for conducting the Gel Bed Permeability Test is shown in FIGS. 1, 2, and 3 and indicated generally as 500. The test apparatus assembly 528 comprises a sample container, generally indicated at 530, and a plunger, generally indicated at 536. The plunger comprises a shaft 538 having a cylinder hole bored down the longitudinal axis and a head 550 positioned at the bottom of the shaft. The shaft hole 562 has a diameter of 16 mm. The plunger head is attached to the shaft, such as by adhesion. Twelve holes 544 are bored into the radial axis of the shaft, three positioned at every 90 degrees having diameters of 6.4 mm. The shaft 538 is machined from a LEXAN rod or equivalent material and has an outer diameter of 2.2 cm and an inner diameter of 16 mm.

The plunger head 550 has a concentric inner ring of seven holes 560 and an outer ring of 14 holes 554, all holes having a diameter of 8.8 millimeters as well as a hole of 16 mm aligned with the shaft. The plunger head 550 is machined from a LEXAN rod or equivalent material and has a height of approximately 16 mm and a diameter sized such that it fits within the cylinder 534 with minimum wall clearance but still slides freely. The total length of the plunger head 550 and shaft 538 is 8.25 cm, but can be machined at the top of the shaft to obtain the desired mass of the plunger 536. The plunger 536 comprises a 100 mesh stainless steel cloth screen 564 that is biaxially stretched to tautness and attached to the lower end of the plunger 536. The screen is attached to the plunger head 550 using an appropriate solvent that causes the screen to be securely adhered to the plunger head 550. Care must be taken to avoid excess solvent migrating into the open portions of the screen and reducing the open area for liquid flow. Acrylic solvent Weld-on 4 from IPS Corporation (having a place of business in Gardena, Calif., USA) is a suitable solvent.

The sample container 530 comprises a cylinder 534 and a 400 mesh stainless steel cloth screen 566 that is biaxially stretched to tautness and attached to the lower end of the cylinder 534. The screen is attached to the cylinder using an appropriate solvent that causes the screen to be securely adhered to the cylinder. Care must be taken to avoid excess solvent migrating into the open portions of the screen and reducing the open area for liquid flow. Acrylic solvent Weld-on 4 from IPS Corporation (having a place of business in Gardena, Calif., USA) is a suitable solvent. A gel particle sample, indicated as 568 in FIG. 2, is supported on the screen 566 within the cylinder 534 during testing.

The cylinder 534 may be bored from a transparent LEXAN rod or equivalent material, or it may be cut from a LEXAN tubing or equivalent material, and has an inner diameter of 6 cm (e.g., a cross-sectional area of 28.27 cm$^2$), a wall thickness of 0.5 cm and a height of approximately 7.95 cm. A step is machined into the outer diameter of the cylinder 534 such that a region 534a with an outer diameter of 66 mm exists for the bottom 31 mm of the cylinder 534. An o-ring 540 which fits the diameter of region 534a may be placed at the top of the step.

The annular weight 548 has a counter-bored hole 2.2 cm in diameter and 1.3 cm deep so that it slips freely onto the shaft 538. The annular weight also has a thru-bore 548a of 16 mm. The annular weight 548 can be made from stainless steel or from other suitable materials resistant to corrosion in the presence of the test solution, which is 0.9 weight percent sodium chloride solution in distilled water. The combined weight of the plunger 536 and annular weight 548 equals approximately 596 grams (g), which corresponds to a pressure applied to the sample 568 of 0.3 pounds per square inch (psi), or 20.7 dynes/cm$^2$ (2.07 kPa), over a sample area of 28.27 cm$^2$.

When the test solution flows through the test apparatus during testing as described below, the sample container 530 generally rests on a weir 600. The purpose of the weir is to divert liquid that overflows the top of the sample container 530 and diverts the overflow liquid to a separate collection device 601. The weir can be positioned above a scale 602 with a beaker 603 resting on it to collect saline solution passing through the swollen sample 568.

To conduct the Gel Bed Permeability Test under "free swell" conditions, the plunger 536, with the weight 548 seated thereon, is placed in an empty sample container 530 and the height from the top of the weight 548 to the bottom of the sample container 530 is measured using a suitable gauge accurate to 0.01 mm. The force the thickness gauge applies during measurement should be as low as possible, preferably less than 0.74 Newtons. It is important to measure the height of each empty sample container 530, plunger 536, and weight 548 combination and to keep track of which plunger 536 and weight 548 is used when using multiple test apparatus. The same plunger 536 and weight 548 should be used for measurement when the sample 568 is later swollen following saturation. It is also desirable that the base that the sample cup 530 is resting on is level, and the top surface of the weight 548 is parallel to the bottom surface of the sample cup 530.

The sample to be tested is prepared from superabsorbent polymer composition particles which are prescreened through a U.S. standard 30 mesh screen and retained on a U.S. standard 50 mesh screen. As a result, the test sample comprises particles sized in the range of 300 to 600 microns. The superabsorbent polymer particles can be pre-screened with, for example, a RO-TAP Mechanical Sieve Shaker Model B available from W. S. Tyler, Inc., Mentor Ohio. Sieving is conducted for 10 minutes. Approximately 2.0 grams of the sample is placed in the sample container 530 and spread out evenly on the bottom of the sample container. The container, with 2.0 grams of sample in it, without the plunger 536 and weight 548 therein, is then submerged in the 0.9% saline solution for a time period of 60 minutes to saturate the sample and allow the sample to swell free of any restraining load. During saturation, the sample cup 530 is set on a mesh located in the liquid reservoir so that the sample cup 530 is raised slightly above the bottom of the liquid reservoir. The mesh does not inhibit the flow of saline solution into the sample cup 530. A suitable mesh can be obtained as part number 7308 from Eagle Supply and Plastic, having a place of business in Appleton, Wis., U.S.A. Saline does not fully cover the superabsorbent polymer composition particles, as would be evidenced by a perfectly flat saline surface in the test cell. Also, saline depth is not allowed to fall so low that the surface within the cell is defined solely by swollen superabsorbent, rather than saline.

At the end of this period, the plunger 536 and weight 548 assembly is placed on the saturated sample 568 in the sample container 530 and then the sample container 530, plunger 536, weight 548, and sample 568 are removed from the solution. After removal and before being measured, the sample container 530, plunger 536, weight 548, and sample 568 are to remain at rest for 30 seconds on a suitable flat, large grid non-deformable plate of uniform thickness. The thickness of the saturated sample 568 is determined by again measuring the height from the top of the weight 548 to the bottom of the sample container 530, using the same thickness gauge used previously provided that the zero point is unchanged from the initial height measurement. The sample container 530, plunger 536, weight 548, and sample 568 may be placed on a flat, large grid non-deformable plate of uniform thickness that will provide for drainage. The plate has an overall dimension of 7.6 cm by 7.6 cm, and each grid has a cell size dimension of 1.59 cm long by 1.59 cm wide by 1.12 cm deep. A suitable flat, large grid non-deformable plate material is a parabolic diffuser panel, catalogue number 1624K27, available from McMaster Carr Supply Company, having a place of business in Chicago, Ill., U.S.A., which can then be cut to the proper dimensions. This flat, large 0 mesh non-deformable plate must also be present when measuring the height of the initial empty assembly. The height measurement should be made as soon as practicable after the thickness gauge is engaged. The height measurement obtained from measuring the empty sample container 530, plunger 536, and weight 548 is subtracted from the height measurement obtained after saturating the sample 568. The resulting value is the thickness, or height "H" of the swollen sample.

The permeability measurement is initiated by delivering a flow of the 0.9% saline solution into the sample container 530 with the saturated sample 568, plunger 536, and weight 548 inside. The flow rate of test solution into the container is adjusted to cause saline solution to overflow the top of the cylinder 534 thereby resulting in a consistent head pressure equal to the height of the sample container 530. The test solution may be added by any suitable means that is sufficient to ensure a small, but consistent amount of overflow from the top of the cylinder, such as with a metering pump 604. The overflow liquid is diverted into a separate collection device 601. The quantity of solution passing through the sample 568 versus time is measured gravimetrically using the scale 602 and beaker 603. Data points from the scale 602 are collected every second for at least sixty seconds once the overflow has begun. Data collection may be taken manually or with data collection software. The flow rate, Q, through the swollen sample 568 is determined in units of grams/second (g/s) by a linear least-square fit of fluid passing through the sample 568 (in grams) versus time (in seconds).

Permeability in cm$^2$ is obtained by the following equation:

$$K=[Q*H*\mu]/[A*\rho*P]$$

where K=Permeability (cm$^2$), Q=flow rate (g/sec), H=height of swollen sample (cm), $\mu$=liquid viscosity (poise) (approximately one centipoise for the test solution used with this Test), A=cross-sectional area for liquid flow (28.27 cm$^2$ for the sample container used with this Test), $\rho$=liquid density (g/cm³) (approximately one g/cm³, for the test solution used with this Test) and P=hydrostatic pressure (dynes/cm²) (normally approximately 7,797 dynes/cm²). The hydrostatic pressure is calculated from $P=\rho*g*h$, where p=liquid density (g/cm³), g=gravitational acceleration, nominally 981 cm/sec², and h=fluid height, e.g., 7.95 cm for the Gel Bed Permeability Test described herein.

A minimum of two samples is tested and the results are averaged to determine the gel bed permeability of the sample.

Absorbency Under Load Test (AUL (0.9 psi))

The Absorbency Under Load (AUL) Test measures the ability of the superabsorbent polymer composition particles to absorb a 0.9 weight percent solution of sodium chloride in distilled water at room temperature (test solution) while the material is under a 0.9 psi load. The apparatus for testing AUL consists of:

An AUL assembly including a cylinder, a 4.4 g piston, and a standard 317 gm weight. The components of this assembly are described in additional detail below.

A flat-bottomed square plastic tray that is sufficiently broad to allow the glass frits to lay on the bottom without contact with the tray walls. A plastic tray that is 9" by 9" (22.9 cm×22.9 cm), with a depth of 0.5 to 1" (1.3 cm to 2.5 cm) is commonly used for this test method.

A 9 cm diameter sintered glass frit with a 'C' porosity (25-50 microns). This frit is prepared in advance through equilibration in saline (0.9% sodium chloride in distilled water, by weight). In addition to being washed with at least two portions of fresh saline, the frit must be immersed in saline for at least 12 hours prior to AUL measurements.

Whatman Grade 1, 9 cm diameter filter paper circles.

A supply of saline (0.9% sodium chloride in distilled water, by weight).

Figure 4:
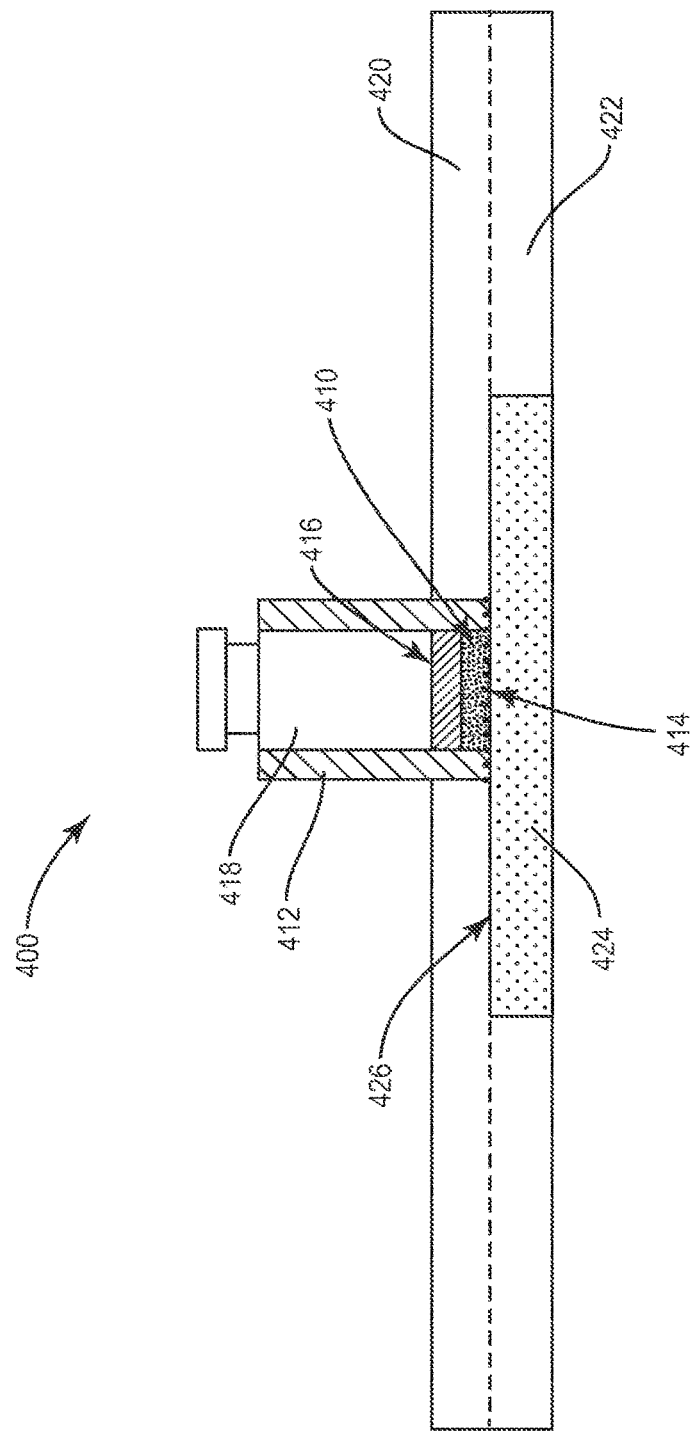
FIG. 4 is a side view of the test apparatus employed for the Absorbency Under Load Test.

Referring to FIG. 4, the cylinder 412 of the AUL assembly 400 used to contain the superabsorbent polymer composition particles 410 is made from one-inch (2.54 cm) inside diameter thermoplastic tubing machined-out slightly to be sure of concentricity. After machining, a 400 mesh stainless steel wire cloth 414 is attached to the bottom of the cylinder 412 by heating the steel wire cloth 414 in a flame until red hot, after which the cylinder 412 is held onto the steel wire cloth until cooled. A soldering iron can be utilized to touch up the seal if unsuccessful or if it breaks. Care must be taken to maintain a flat smooth bottom and not distort the inside of the cylinder 412.

The 4.4 g piston (416) is made from one-inch diameter solid material (e.g., PLEXIGLAS®) and is machined to closely fit without binding in the cylinder 412.

A standard 317 gm weight 418 is used to provide a 62,053 dyne/cm² (0.9 psi) restraining load. The weight is a cylindrical, 1 inch (2.5 cm) diameter, stainless steel weight that is machined to closely fit without binding in the cylinder.

Unless specified otherwise, a sample 410 corresponding to a layer of at least 300 gsm. (0.16 g) of superabsorbent polymer composition particles is utilized for testing the AUL. The sample 410 is taken from superabsorbent polymer composition particles that are pre-screened through U.S. standard #30 mesh and retained on U.S. std. #50 mesh. The superabsorbent polymer composition particles can be pre-screened with, for example, a RO-TAP® Mechanical Sieve Shaker Model B available from W. S. Tyler, Inc., Mentor Ohio. Sieving is conducted for 10 minutes.

The inside of the cylinder 412 is wiped with an antistatic cloth prior to placing the superabsorbent polymer composition particles 410 into the cylinder 412.

The desired amount of the sample of sieved superabsorbent polymer composition particles 410 (0.16 g) is weighed out on a weigh paper and evenly distributed on the wire cloth 414 at the bottom of the cylinder 412. The weight of the superabsorbent polymer composition particles in the bottom of the cylinder is recorded as 'SA,' for use in the AUL calculation described below. Care is taken to be sure no superabsorbent polymer particles cling to the wall of the cylinder. After carefully placing the 4.4 g piston 412 and 317 g weight 418 on the superabsorbent polymer composition particles 410 in the cylinder 412, the AUL assembly 400 including the cylinder, piston, weight, and superabsorbent polymer composition particles is weighed, and the weight is recorded as weight 'A'.

A sintered glass frit 424 (described above) is placed in the plastic tray 420, with saline 422 added to a level equal to that of the upper surface of the glass frit 424. A single circle of filter paper 426 is placed gently on the glass frit 424, and the AUL assembly 400 with the superabsorbent polymer composition particles 410 is then placed on top of the filter paper 426. The AUL assembly 400 is then allowed to remain on top of the filter paper 426 for a test period of one hour, with attention paid to keeping the saline level in the tray constant. At the end of the one hour test period, the AUL apparatus is then weighed, with this value recorded as weight 'B.'

The AUL (0.9 psi) is calculated as follows:

$$\mathrm{AUL}(0.9\ \mathrm{psi}) = (B-A)/SA$$

wherein
A=Weight of AUL Unit with dry SAP
B=Weight of AUL Unit with SAP after 60 minutes absorption
SA=Actual SAP weight A minimum of two tests is performed and the results are averaged to determine the AUL value under 0.9 psi load. The samples are tested at 23° C. and 50% relative humidity.

Absorption at Pressure at 0.7 psi (AAP (0.7 psi) Test

The absorption at pressure at 0.7 psi (pressure load 50 g/cm²) is determined by a method described in EP 0 339 461, p. 7. Approximately 0.9 g of particulate superabsorbent polymer composition is weighed into a cylinder with a sieve plate. The uniformly scattered particulate superabsorbent polymer composition layer is placed under load in the form of a plunger exerting a pressure of 0.7 psi or 50 g/cm². The pre-weighed cylinder is then placed on a glass filter disk standing in a bowl containing 0.9% NaCl solution, the liquid level of which corresponds precisely to the height of the filter disk. After the cylinder unit has been left to soak up 0.9% NaCl solution for 1 hour, this is re-weighed, and the AAP is calculated as follows: AAP=amount weighed out (cylinder unit+particulate superabsorbent polymer composition)-amount weighed in (cylinder unit+particulate superabsorbent polymer composition soaked to capacity)/amount of particulate superabsorbent polymer composition weighed in.

Saline Flow Conductivity (SFC) Test

Permeability to a 0.9% common salt solution in the swollen state (SFC)

Permeability in the swollen state (SFC test, according to WO 95/22356). Approximately 0.9 g particulate superabsorbent polymer composition is weighed into a cylinder having a sieve plate and is distributed carefully on the surface of the sieve. The particulate superabsorbent polymer composition is allowed to swell for 1 hour against an opposing pressure of 20 g/cm² in JAYCO synthetic urine [composition: 2.0 g potassium chloride; 2.0 g sodium sulfate; 0.85 g ammonium dihydrogen phosphate; 0.15 g ammonium hydrogen phosphate; 0.19 g calcium chloride; 0.23 g magnesium chloride as anhydrous salts dissolved in 1 liter distilled water]. After determining the swollen height of the superabsorber, 0.118 M NaCl solution is run through the swollen gel layer from a leveled supply vessel at constant hydrostatic pressure. The swollen gel layer is covered during measurement with a special sieve cylinder which guarantees a uniform distribution of the 0.118 M NaCl solution above the gel and constant conditions (measuring temperature 20-25° C.) during measurement in relation to the gel bed state. The pressure acting on the swollen particulate superabsorbent polymer composition continues at 20 g/cm². With the aid of a computer and scales the quantity of liquid which passes through the gel layer as a function of time is determined at 20-second intervals within a period of 10 minutes. Using regression analysis, the flow rate, g/s, through the swollen gel layer at t=0 is determined at the mid-point of the flow quantity between minutes 2 and 10 by extrapolation of the gradient.

The SFC value (K) is calculated as follows:

$$K=F_s(t=0) \cdot L_o/(r \cdot A \cdot \Delta P)=F_s(t=0) \cdot L_o/(139506)$$

wherein: $F_s(t=0)$ flow rate in g/s $L_0$ is the thickness of the gel layer, in cm r is the density of the NaCl solution (1.003 g/cm³)

A is the area of the upper surface of the gel layer in the measuring cylinder (28.27 cm²)

$\Delta P$ is the hydrostatic pressure bearing on the gel layer (4920 dyne/cm²) and K is the SFC value $[10^{-7} *cm^3 *s*g^{-1}]$.

EXAMPLES

The following comparative examples and examples, and preproduct therefore, are provided to illustrate the invention and do not limit the scope of the claims. Unless otherwise stated all parts, and percentages are by weight.

Crosslinker 1: (EDA+4AGE) Ethylenediamine-AGE

Ethylenediamine (60.1 g) and water (10.0 g) are reacted with allylglycidyl ether (456.2 g) at 80° C. The clear and slightly yellow product is an adduct of ethylenediamine with 4.0 mol allylglycidyl ether.

Crosslinker 2: (EDA+4AGE+0.035% SR454) Ethylenediamine-AGE Adduct

Ethylenediamine (60.1 g) and water (10.0 g) are reacted with allylglycidyl ether (456.2 g) at 80° C. The clear and slightly yellow product is an adduct of ethylenediamine with 4.0 mol allylglycidyl ether. The Ethylenediamine-AGE Adduct was added to the monomer mixture followed by addition of the 0.035 wt % of SR454 which is an ethoxylated (3) trimethylolpropane triacrylate available from the Sartomer Company of Easton Pa. right before polymerization.

Crosslinker 3: (EDA+4AGE+0.5PO) Ethylenediamine-AGE-PO

Ethylenediamine (60.1 g) and water (10.0 g) are reacted with allylglycidyl ether (456.2 g) at 80° C. After 4 hours of post reaction propylene oxide (27.4 g) is charged into the vessel within 2 min. The mixture is agitated at 80° C. for 75 min, then heated to 110° C. Water and unreacted propylene oxide are distilled off under vacuum (20 mbar), and the final product is cooled to room temperature. The clear and slightly yellow product is an adduct of ethylenediamine with 4.0 mol allylglycidyl ether.

Crosslinker 4: (EDA+4AGE+0.5PO+0.035% SR454) Ethylenediamine-AGE-PO Adduct

The procedure described in Crosslinker 3 is repeated and added to the monomer and the 0.035 wt % of SR454 which is an ethoxylated (3) trimethylolpropane triacrylate available from the Sartomer Company of Easton Pa. was added right before polymerization.

Crosslinker 5: (Diallylamine-AGE)

Diallylamine (97.1 g) and water (3.0 g) are reacted with allylglycidyl ether (102.6 g) at 100° C. for 4.5 hours. Water and remaining diallylamine are distilled off at 115° C. under vacuum. The clear and slightly yellow product is an adduct of diallylamine with 0.9 mol allylglycidyl ether.

Crosslinker 6: (Diallylamine-AGE+0.035% SR454)

The procedure described in Crosslinker 5 is repeated and the 0.035 wt % of SR454 which is an ethoxylated (3) trimethylolpropane triacrylate available from the Sartomer Company of Easton Pa. was added right before polymerization.

Crosslinker 7: (Diallylamine-AGE-PO)

Diallylamine (97.1 g) and water (3.0 g) are reacted with allylglycidyl ether (102.6 g) at 100° C. for 4.5 hours. Propylene oxide (17.4 g) is charged into the vessel. After another post reaction of 70 min at 100° C. water and remaining propylene oxide are distilled off at 115° C. under vacuum. The clear and slightly yellow product is a composition of adducts from diallylamine with allylglycidyl ether and with propylene oxide.

Crosslinker 8: (Diallylamine-AGE-PO+0.035% SR454)

The procedure described in Crosslinker 7 is repeated and added to the monomer and the 0.035 wt % of SR454 which is an ethoxylated (3) trimethylolpropane triacrylate available from the Sartomer Company of Easton Pa. was added right before polymerization.

Crosslinker 9: (HMDA-AGE)

Hexamethylenediamine (116.1 g) and water (10.0 g) are reacted with allylglycidyl ether (456.2 g) at 80° C. The clear and slightly yellow product is an adduct of hexamethylenediamine with 4.0 mol allylglycidyl ether is a crosslinker composition of the present invention.

Crosslinker 10: (Diallylamine-AGE+0.035% SR454)

The procedure described in Crosslinker 9 is repeated and added to the monomer and the 0.035 wt % of SR454 which is an ethoxylated (3) trimethylolpropane triacrylate available from the Sartomer Company of Easton Pa. was added right before polymerization.

Crosslinker 11: (HMDA-AGE-PO)

Hexamethylenediamine (116.1 g) and water (10.0 g) are reacted with allylglycidyl ether (456.2 g) at 80° C. After 4 hours of post reaction propylene oxide (23.2 g) is charged into the vessel. After another post reaction of 60 min at 80° C. water and residual propylene oxide are removed by vacuum distillation at 115° C. The clear and slightly yellow product is an adduct of hexamethylenediamine with 3.8 mol allylglycidyl ether and 0.2 mol propylene oxide is a crosslinker composition of the present invention.

Crosslinker 12: (Diallylamine-AGE-PO+0.035% SR454)

The procedure described in Crosslinker 11 is repeated and the 0.035 wt % of SR454 which is an ethoxylated (3) trimethylolpropane triacrylate available from the Sartomer Company of Easton Pa. was added right before polymerization.

Particulate Superabsorbent Polymer Composition

The particulate superabsorbent polymer composition is made as follows. Into a polyethylene container equipped with an agitator and cooling coils was added 482 grams of 50% NaOH and 821 grams of distilled water and cooled to 20° C. 207 grams of glacial acrylic acid was then added to the caustic solution and the solution again cooled to 20° C. The degree of neutralization of the acidic groups was 75 mol %. The internal crosslinker composition and specific amount of internal crosslinker composition, in accordance with Tables 1-12 below, and 413 grams of glacial acrylic acid were added to the first solution, followed by cooling to 4-6° C. Nitrogen was bubbled through the monomer solution for 10 minutes. The cooling coils were removed from the container. To the monomer solution was added 20 g of 1% by weight of $H_2O_2$ aqueous solution, 30 g of 2 wt % aqueous sodium persulfate solution, and 18 g of 0.5 wt % aqueous sodium erythorbate solution to initiate polymerization reaction. The agitator was stopped and the initiated monomer was allowed to polymerize for 20 minutes. The solids content of the materials was 30%. The resulting hydrogel was chopped and extruded with a Hobart 4M6 commercial extruder, followed by drying in a Procter & Schwartz Model 062 forced air oven at 150° C. for 120 minutes with up flow and 6 minutes with down flow air on a 20 in×40 in perforated metal tray to a final product moisture level of less than 5 wt %. The dried particulate superabsorbent polymer composition was coarse-ground in a Prodeva Model 315-S crusher, milled in an MPI 666-F three-stage roller mill and sieved with a Minox MTS 600DS3V to remove particles greater than 850 μm and smaller than 150 μm.

Examples 1 to 240 and Comparative Examples 1-36

In accordance with Tables 1 to 12 including Examples 1 to 240, and Comparative Examples C1-C36, the Internal Crosslinkers Compositions 1-12, were added into the monomer solution of the superabsorbent polymer composition for Examples 1 to 240 and the particulate superabsorbent polymer was further processed with surface crosslinking and optionally surface treatment as shown in the tables below.

The following nomenclature for the particulate superabsorbent polymer composition is used in the following tables: SX means surface crosslink; Pre-treatment before SX means application of elements onto the superabsorbent polymer particle surface; Post-treatment after SX means surface treatment of the surface crosslinked superabsorbent polymer particles; and EC means ethylene carbonate. The units of the properties of the particulate superabsorbent polymer composition are CRC (g/g); AUL (0.9 psi) (g/g); GBP (Darcy); AAP (0.7 psi) (g/g) and SFC ($10^{-7}*cm^3*s*g^{-1}$). All % in the table means wt % as defined herein.

TABLE 1

Comparative Examples C1-C3 and Examples 1-20
0.3 wt. % of Internal Crosslinker 1 (4 molAGE/1 molEDA) was added to the solution as set forth in making the Particulate Superabsorbent Polymer Composition and the resulting particulate superabsorbent polymer was surface crosslinked and surface treated as set forth in Table 1 to form Examples 1-20 of the particulate superabsorbent polymer composition.

| | Pre-Treatment before SX | | | | | SX step | | Post-treatment after SX | | | | Properties | | | | |
|---|---|---|---|---|---|---|---|---|---|---|---|---|---|---|---|---|
| No. | EC | Water | Silica | Al-lactate | Al-Sulfate | Temperature | Time min | Water | Silica | Al-lactate | Al-Sulfate | CRC | AUL (0.9 psi) | GBP | AAP (0.7 psi) | SFC |
| C1 | | | | PSXM sample, no surface-crosslinking or additives | | | | | | | | 34 | | | | |
| C2 | 1% | 3% | — | — | — | 180° C. | 30 | — | — | — | — | 28.1 | 23.6 | 21 | 25.2 | 31 |
| C3 | 1% | 3% | — | — | — | 170° C. | 90 | — | — | — | — | 27.8 | 24.1 | 17 | 25.5 | 52 |
| 1 | 1% | 3% | — | 0.3% | — | 180° C. | 30 | — | — | — | — | 28.5 | 23.2 | 21 | 25.4 | 72 |
| 2 | 1% | 3% | — | 0.3% | — | 170° C. | 90 | — | — | — | — | 28.8 | 23.6 | 13 | 25.9 | 55 |
| 3 | 1% | 3% | — | — | 0.3% | 180° C. | 30 | — | — | — | — | 27.6 | 23.0 | 24 | 24.9 | 51 |
| 4 | 1% | 3% | — | — | 0.3% | 170° C. | 90 | — | — | — | — | 28.4 | 22.6 | 22 | 25.4 | 43 |
| 5 | 1% | 3% | 0.5% | — | — | 180° C. | 30 | — | — | — | — | 27.5 | 20.7 | 99 | 22.8 | 114 |
| 6 | 1% | 3% | 0.5% | — | — | 170° C. | 90 | — | — | — | — | 27.9 | 20.4 | 90 | 22.0 | 141 |
| 7 | 1% | 3% | 0.5% | 0.3% | — | 180° C. | 30 | — | — | — | — | 28.1 | 20.1 | 98 | 21.7 | — |
| 8 | 1% | 3% | 0.5% | 0.3% | — | 170° C. | 90 | — | — | — | — | 28.0 | 20.1 | 114 | 21.9 | — |
| 9 | 1% | 3% | 0.5% | — | 0.3% | 180° C. | 30 | — | — | — | — | 27.1 | 20.4 | 131 | 21.2 | — |
| 10 | 1% | 3% | 0.5% | — | 0.3% | 170° C. | 90 | — | — | — | — | 27.9 | 20.5 | 101 | 22.1 | — |
| 11 | 1% | 3% | 0.5% | 0.15% | 0.15% | 180° C. | 30 | — | — | — | — | 27.5 | 20.4 | 75 | 22.5 | — |
| 12 | 1% | 3% | 0.5% | 0.15% | 0.15% | 170° C. | 90 | — | — | — | — | 28.5 | 20.1 | 76 | 22.5 | — |
| 13 | 1% | 3% | — | — | — | 180° C. | 30 | — | — | — | — | 27.7 | 21.3 | 62 | 22.9 | 84 |
| 14 | 1% | 3% | — | — | — | 170° C. | 90 | — | — | — | — | 28.7 | 21.9 | 39 | 23.8 | 74 |
| 15 | 1% | 3% | — | — | — | 180° C. | 30 | 4% | — | — | — | 26.4 | 20.0 | 51 | 21.5 | — |
| 16 | 1% | 3% | — | — | — | 170° C. | 90 | 4% | — | — | — | 26.3 | 20.1 | 80 | 22.2 | — |
| 17 | 1% | 3% | — | — | — | 180° C. | 30 | 4% | — | — | 0.3% | 26.6 | 20.4 | 59 | 22.1 | — |
| 18 | 1% | 3% | — | — | — | 170° C. | 90 | 4% | — | — | 0.3% | 26.5 | 20.4 | 72 | 22.2 | — |
| 19 | 1% | 3% | — | — | — | 180° C. | 30 | 4% | — | — | 0.15% | 26.9 | 20.3 | 46 | 20.9 | — |
| 20 | 1% | 3% | — | — | — | 170° C. | 90 | 4% | — | — | 0.15% | 26.9 | 20.2 | 61 | 22.0 | — |

TABLE 2

Comparative Examples C4-C6 and Examples 21-40
0.3 wt. % of Internal Crosslinker 2 (4 molAGE/1 molEDA) and 0.035% SR 454) was added to the solution as set forth in making the Particulate Superabsorbent Polymer Composition and the resulting particulate superabsorbent polymer was surface crosslinked and surface treated as set forth in Table 2 to form Examples 21-40 of the particulate superabsorbent polymer composition.

| | Pre-Treatment before SX | | | | SX step | | Post-treatment after SX | | | | Properties | | | | |
|---|---|---|---|---|---|---|---|---|---|---|---|---|---|---|---|
| No. | EC | Water | Silica | Al-lactate | Al-Sulfate | Temperature | Time min | Water | Silica | Al-lactate | Al-Sulfate | CRC | AUL (0.9 psi) | GBP | AAP (0.7 psi) | SFC |
| C4 | PSXM sample, no surface-crosslinking or additives | | | | | | | | | | | 32.6 | | | | |
| C5 | 1% | 3% | — | — | — | 180° C. | 30 | —% | —% | —% | —% | 27.2 | 23.2 | 13 | 25.5 | 40 |
| C6 | 1% | 3% | — | — | — | 170° C. | 90 | — | — | — | — | 27.7 | 23.6 | 13 | 25.7 | 51 |
| 21 | 1% | 3% | — | 0.3% | — | 180° C. | 30 | — | — | — | — | 27.4 | 22.5 | 11 | 24.7 | 58 |
| 22 | 1% | 3% | — | 0.3% | — | 170° C. | 90 | — | — | — | — | 27.6 | 23.0 | 12 | 24.9 | 61 |
| 23 | 1% | 3% | — | — | 0.3% | 180° C. | 30 | — | — | — | — | 26.8 | 22.0 | 28 | 24.3 | 79 |
| 24 | 1% | 3% | — | — | 0.3% | 170° C. | 90 | — | — | — | — | 26.8 | 22.2 | 32 | 24.1 | 67 |
| 25 | 1% | 3% | 0.5% | — | — | 180° C. | 30 | — | — | — | — | 26.6 | 19.5 | 101 | 22.6 | 98 |
| 26 | 1% | 3% | 0.5% | — | — | 170° C. | 90 | — | — | — | — | 27.1 | 19.7 | 85 | 22.7 | 115 |
| 27 | 1% | 3% | 0.5% | 0.3% | — | 180° C. | 30 | — | — | — | — | 27.1 | 20.3 | 120 | 22.2 | — |
| 28 | 1% | 3% | 0.5% | 0.3% | — | 170° C. | 90 | — | — | — | — | 27.6 | 19.8 | 109 | 21.9 | — |
| 29 | 1% | 3% | 0.5% | —% | 0.3% | 180° C. | 30 | — | — | — | — | 27.0 | 19.2 | 123 | 22.5 | — |
| 30 | 1% | 3% | 0.5% | —% | 0.3% | 170° C. | 90 | — | — | — | — | 27.1 | 20.7 | 127 | 22.8 | — |
| 31 | 1% | 3% | 0.5% | 0.15% | 0.15% | 180° C. | 30 | — | — | — | — | 26.6 | 19.9 | 131 | 22.8 | — |
| 32 | 1% | 3% | 0.5% | 0.15% | 0.15% | 170° C. | 90 | — | — | — | — | 27.4 | 20.0 | 111 | 22.8 | — |
| 33 | 1% | 3% | — | — | — | 180° C. | 30 | — | 0.5% | —% | — | 27.6 | 21.3 | 47 | 23.7 | 71 |
| 34 | 1% | 3% | — | — | — | 170° C. | 90 | — | 0.5% | —% | — | 27.8 | 21.9 | 53 | 23.0 | 75 |
| 35 | 1% | 3% | — | — | — | 180° C. | 30 | 4% | 0.5% | 0.3% | — | 27.2 | 19.4 | 75 | 22.1 | — |
| 36 | 1% | 3% | — | — | — | 170° C. | 90 | 4% | 0.5% | 0.3% | — | 26.4 | 19.8 | 71 | 22.0 | — |
| 37 | 1% | 3% | — | — | — | 180° C. | 30 | 4% | 0.5% | — | — | 26.5 | 20.8 | 78 | 22.4 | — |
| 38 | 1% | 3% | — | — | — | 170° C. | 90 min | 4% | 0.5% | — | — | 27.0 | 20.0 | 111 | 21.9 | — |
| 39 | 1% | 3% | — | — | — | 180° C. | 30 | 4% | 0.5% | 0.15 | — | 26.7 | 19.2 | 69 | 22.2 | — |
| 40 | 1% | 3% | — | — | — | 170° C. | 90 | 4% | 0.5% | 0.15% | — | 27.0 | 19.9 | 81 | 21.8 | — |

TABLE 3

Comparative Examples C7-C9 and Examples 41-60
0.3 wt. % of Internal Crosslinker 3 (4 molAGE/1 molEDA + 0.5 molPO) was added to the solution as set forth in making the Particulate Superabsorbent Polymer Composition and the resulting particulate superabsorbent polymer was surface crosslinked and surface treated as set forth in Table 3 to form Examples 41-60 of the particulate superabsorbent polymer composition.

| | Pre-Treatment before SX | | | | SX step | | Post-treatment after SX | | | | Properties | | | | |
|---|---|---|---|---|---|---|---|---|---|---|---|---|---|---|---|
| No. | EC | Water | Silica | Al-lactate | Al-Sulfate | Temperature | Time min | Water | Silica | Al-lactate | Al-Sulfate | CRC | AUL (0.9 psi) | GBP | AAP (0.7 psi) | SFC |
| C7 | PSXM sample, no surface-crosslinking or additives | | | | | | | | | | | 34.7 | | | | |
| C8 | 1% | 3% | — | — | — | 180° C. | 30 | — | — | — | — | 28.3 | 23.5 | 10 | 25.2 | 33 |
| C9 | 1% | 3% | — | — | — | 170° C. | 90 | — | — | — | — | 28.2 | 23.4 | 11 | 25.6 | 43 |
| 41 | 1% | 3% | — | 0.3% | — | 180° C. | 30 | — | — | — | — | 28.2 | 22.8 | 5 | 24.9 | 23 |
| 42 | 1% | 3% | — | 0.3% | — | 170° C. | 90 | — | — | — | — | 28.1 | 23.3 | 6 | 25.1 | 51 |
| 43 | 1% | 3% | — | — | 0.3% | 180° C. | 30 | — | — | — | — | 28.1 | 22.1 | 14 | 24.1 | 47 |
| 44 | 1% | 3% | — | — | 0.3% | 170° C. | 90 | — | — | — | — | 27.9 | 23.1 | 39 | 24.0 | 95 |
| 45 | 1% | 3% | 0.5% | — | — | 180° C. | 30 | — | — | — | — | 28.3 | 19.9 | 72 | 21.5 | 100 |
| 46 | 1% | 3% | 0.5% | — | — | 170° C. | 90 | — | — | — | — | 28.5 | 20.1 | 104 | 21.6 | 100 |
| 47 | 1% | 3% | 0.5% | 0.3% | — | 180° C. | 30 | — | — | — | — | 28.0 | 19.6 | 108 | 21.7 | — |
| 48 | 1% | 3% | 0.5% | 0.3% | — | 170° C. | 90 | — | — | — | — | 28.4 | 19.8 | 107 | 21.4 | — |
| 49 | 1% | 3% | 0.5% | — | 0.3% | 180° C. | 30 | — | — | — | — | 27.5 | 19.8 | 116 | 21.8 | — |
| 50 | 1% | 3% | 0.5% | — | 0.3% | 170° C. | 90 | — | — | — | — | 27.9 | 20.1 | 141 | 22.0 | — |
| 51 | 1% | 3% | 0.5% | 0.15% | 0.15% | 180° C. | 30 | — | — | — | — | 28.0 | 19.5 | 90 | 21.6 | — |
| 52 | 1% | 3% | 0.5% | 0.15% | 0.15% | 170° C. | 90 | — | — | — | — | 28.0 | 20.6 | 105 | 22.5 | — |
| 53 | 1% | 3% | — | — | — | 180° C. | 30 | — | 0.5% | — | — | 27.8 | 21.3 | 41 | 23.0 | 58 |
| 54 | 1% | 3% | — | — | — | 170° C. | 90 | — | 0.5% | — | — | 28.2 | 21.7 | 35 | 23.5 | 66 |
| 55 | 1% | 3% | — | — | — | 180° C. | 30 | 4% | 0.5% | 0.3% | — | 27.0 | 19.1 | 49 | 21.0 | — |
| 56 | 1% | 3% | — | — | — | 170° C. | 90 | 4% | 0.5% | 0.3% | — | 27.3 | 19.2 | 79 | 21.4 | — |
| 57 | 1% | 3% | — | — | — | 180° C. | 30 | 4% | 0.5% | — | 0.3% | 27.5 | 19.7 | 61 | 21.9 | — |
| 58 | 1% | 3% | — | — | — | 170° C. | 90 | 4% | 0.5% | — | 0.3% | 27.1 | 19.9 | 90 | 22.1 | — |
| 59 | 1% | 3% | — | — | — | 180° C. | 30 | 4% | 0.5% | 0.15% | 0.15% | 27.1 | 19.3 | 56 | 21.3 | — |
| 60 | 1% | 3% | — | — | — | 170° C. | 90 | 4% | 0.5% | 0.15% | 0.15% | 27.1 | 20.0 | 63 | 21.5 | — |

TABLE 4

Comparative Examples C10-C12 and Examples 61-80
0.3 wt. % of Internal Crosslinker 4 (4 molAGE/1 molEDA + 0.5 molPO and 0.035 wt. % SR 454) was added to the solution as set forth in making the Particulate Superabsorbent Polymer Composition and the resulting particulate superabsorbent polymer was surface crosslinked and surface treated as set forth in Table 4 to form Examples 61-80 of the particulate superabsorbent polymer composition.

| | Pre-Treatment before SX | | | | SX step | | Post-treatment after SX | | | | Properties | | | | |
|---|---|---|---|---|---|---|---|---|---|---|---|---|---|---|---|
| No. | EC | Water | Silica | Al-lactate | Al-Sulfate | Temperature | Time min | Water | Silica | Al-lactate | Al-Sulfate | CRC | AUL (0.9 psi) | GBP | AAP (0.7 psi) | SFC |
| C10 | | | | | PSXM sample, no surface-crosslinking or additives | | | | | | | 32.7 | | | | |
| C11 | 1% | 3% | — | — | — | 180° C. | 30 | — | — | — | — | 27.6 | 23.2 | 11 | 25.3 | 28 |
| C12 | 1% | 3% | — | — | — | 170° C. | 90 | — | — | — | — | 28.1 | 23.3 | 11 | 25.2 | 42 |
| 61 | 1% | 3% | — | 0.3% | — | 180° C. | 30 | — | — | — | — | 28.4 | 23.1 | 12 | 24.6 | 36 |
| 62 | 1% | 3% | — | 0.3% | — | 170° C. | 90 min | — | — | — | — | 27.8 | 23.8 | 20 | 24.6 | 97 |
| 63 | 1% | 3% | — | — | 0.3% | 180° C. | 30 | — | — | — | — | 27.9 | 22.4 | 37 | 23.8 | 72 |
| 64 | 1% | 3% | — | — | 0.3% | 170° C. | 90 | — | — | — | — | 27.5 | 22.8 | 34 | 24.0 | 77 |
| 65 | 1% | 3% | 0.5% | — | — | 180° C. | 30 | — | — | — | — | 27.2 | 19.5 | 96 | 22.3 | 138 |
| 66 | 1% | 3% | 0.5% | — | — | 170° C. | 90 | — | — | — | — | 27.3 | 20.0 | 108 | 21.3 | 124 |
| 67 | 1% | 3% | 0.5% | 0.3% | — | 180° C. | 30 | — | — | — | — | 28.6 | 18.9 | 75 | 21.4 | — |
| 68 | 1% | 3% | 0.5% | 0.3% | — | 170° C. | 90 | — | — | — | — | 28.0 | 19.9 | 88 | 22.2 | — |
| 69 | 1% | 3% | 0.5% | — | 0.3% | 180° C. | 30 | — | — | — | — | 27.7 | 19.9 | 84 | 21.8 | — |
| 70 | 1% | 3% | 0.5% | — | 0.3% | 170° C. | 90 | — | — | — | — | 27.5 | 20.4 | 118 | 22.3 | — |
| 71 | 1% | 3% | 0.5% | 0.15% | 0.15% | 180° C. | 30 | — | — | — | — | 27.6 | 19.9 | 94 | 22.3 | — |
| 72 | 1% | 3% | 0.5% | 0.15% | 0.15% | 170° C. | 90 | — | — | — | — | 27.6 | 19.9 | 55 | 22.2 | — |
| 73 | 1% | 3% | — | — | — | 180° C. | 30 | — | 0.5% | — | — | 27.7 | 20.1 | 56 | 22.4 | 61 |
| 74 | 1% | 3% | — | — | — | 170° C. | 90 | — | 0.5% | — | — | 28.3 | 20.3 | 70 | 22.4 | 90 |
| 75 | 1% | 3% | — | — | — | 180° C. | 30 | 4% | 0.5% | 0.3% | — | 26.3 | 19.0 | 63 | 21.6 | — |
| 76 | 1% | 3% | — | — | — | 170° C. | 90 | 4% | 0.5% | 0.3% | — | 26.8 | 19.2 | 53 | 21.4 | — |
| 77 | 1% | 3% | — | — | — | 180° C. | 30 | 4% | 0.5% | — | 0.3% | 26.5 | 20.2 | 62 | 21.9 | — |
| 78 | 1% | 3% | — | — | — | 170° C. | 90 | 4% | 0.5% | — | 0.3% | 27.0 | 20.0 | 72 | 21.3 | — |
| 79 | 1% | 3% | — | — | — | 180° C. | 30 | 4% | 0.5% | 0.15% | 0.15% | 26.6 | 19.8 | 57 | 21.7 | — |
| 80 | 1% | 3% | — | — | — | 170° C. | 90 | 4% | 0.5% | 0.15% | 0.15% | 27.0 | 19.7 | 62 | 21.5 | — |

TABLE 5

Comparative Examples C13-C15 and Examples 81-100
0.3 wt. % of Internal Crosslinker 5 (1 molAGE/1 molDAA) was added to the solution as set forth in making the Particulate Superabsorbent Polymer Composition and the resulting particulate superabsorbent polymer was surface crosslinked and surface treated as set forth in Table 5 to form Examples 81-100 of the particulate superabsorbent polymer composition.

| | Pre-Treatment before SX | | | | SX step | | Post-treatment after SX | | | | Properties | | | | |
|---|---|---|---|---|---|---|---|---|---|---|---|---|---|---|---|
| No. | EC | Water | Silica | Al-lactate | Al-Sulfate | Temperature | Time min | Water | Silica | Al-lactate | Al-Sulfate | CRC | AUL (0.9 psi) | GBP | AAP (0.7 psi) | SFC |
| C13 | | | | | PSXM sample, no surface-crosslinking or additives | | | | | | | 32.9 | | | | |
| C14 | 1% | 3% | — | — | — | 180° C. | 30 | — | — | — | — | 28.0 | 23.5 | 12 | 24.9 | 39 |
| C15 | 1% | 3% | — | — | — | 170° C. | 90 | — | — | — | — | 28.6 | 23.8 | 14 | 25.3 | 57 |
| 81 | 1% | 3% | — | 0.3% | — | 180° C. | 30 | — | — | — | — | 28.2 | 23.0 | 7 | 24.5 | 54 |
| 82 | 1% | 3% | — | 0.3% | — | 170° C. | 90 | — | — | — | — | 28.1 | 23.5 | 7 | 24.6 | 46 |
| 83 | 1% | 3% | — | — | 0.3% | 180° C. | 30 | — | — | — | — | 27.8 | 22.3 | 34 | 23.6 | 54 |
| 84 | 1% | 3% | — | — | 0.3% | 170° C. | 90 | — | — | — | — | 28.3 | 22.0 | 21 | 24.4 | 59 |
| 85 | 1% | 3% | 0.5% | — | — | 180° C. | 30 | — | — | — | — | 27.2 | 19.4 | 72 | 21.9 | 134 |
| 86 | 1% | 3% | 0.5% | — | — | 170° C. | 90 | — | — | — | — | 28.1 | 19.9 | 69 | 21.8 | 143 |
| 87 | 1% | 3% | 0.5% | 0.3% | — | 180° C. | 30 | — | — | — | — | 27.8 | 19.8 | 76 | 21.7 | — |
| 88 | 1% | 3% | 0.5% | 0.3% | — | 170° C. | 90 | — | — | — | — | 28.4 | 19.4 | 86 | 22.1 | — |
| 89 | 1% | 3% | 0.5% | — | 0.3% | 180° C. | 30 | — | — | — | — | 26.7 | 19.6 | 102 | 21.5 | — |
| 90 | 1% | 3% | 0.5% | — | 0.3% | 170° C. | 90 | — | — | — | — | 27.3 | 19.9 | 114 | 22.1 | — |
| 91 | 1% | 3% | 0.5% | 0.15% | 0.15% | 180° C. | 30 | — | — | — | — | 27.7 | 20.2 | 99 | 22.1 | — |
| 92 | 1% | 3% | 0.5% | 0.15% | 0.15% | 170° C. | 90 | — | — | — | — | 28.8 | 20.3 | 64 | 22.1 | — |
| 93 | 1% | 3% | — | — | — | 180° C. | 30 | — | 0.5% | — | — | 28.1 | 20.0 | 62 | 21.8 | 83 |
| 94 | 1% | 3% | — | — | — | 170° C. | 90 | — | 0.5% | — | — | 28.6 | 20.1 | 69 | 22.3 | 62 |
| 95 | 1% | 3% | — | — | — | 180° C. | 30 | 4% | 0.5% | 0.3% | — | 27.1 | 19.8 | 55 | 21.7 | — |
| 96 | 1% | 3% | — | — | — | 170° C. | 90 | 4% | 0.5% | 0.3% | — | 27.5 | 19.5 | 61 | 21.7 | — |
| 97 | 1% | 3% | — | — | — | 180° C. | 30 | 4% | 0.5% | — | 0.3% | 27.0 | 19.7 | 70 | 21.5 | — |
| 98 | 1% | 3% | — | — | — | 170° C. | 90 | 4% | 0.5% | — | 0.3% | 27.3 | 19.7 | 70 | 21.8 | — |
| 99 | 1% | 3% | — | — | — | 180° C. | 30 | 4% | 0.5% | 0.15% | 0.15% | 26.8 | 21.4 | 52 | 21.6 | — |
| 100 | 1% | 3% | — | — | — | 170° C. | 90 | 4% | 0.5% | 0.15% | 0.15% | 27.2 | 19.4 | 48 | 21.8 | — |

TABLE 6

Comparative Examples C16-C18 and Examples 101-120
0.3 wt. % of Internal Crosslinker 6 (1 molAGE/1 molDAA and 0.035 wt. % SR454) was added to the solution as set forth in making the Participate Superabsorbent Polymer Composition and the resulting particulate superabsorbent polymer was surface crosslinked and surface treated as set forth in Table 6 to form Examples 101-120 of the particulate superabsorbent polymer composition.

| | Pre-Treatment before SX | | | | SX step | | Post-treatment after SX | | | | Properties | | | | |
|---|---|---|---|---|---|---|---|---|---|---|---|---|---|---|---|
| No. | EC | Water | Silica | Al-lactate | Al-Sulfate | Temperature | Time min | Water | Silica | Al-lactate | Al-Sulfate | CRC | AUL (0.9 psi) | GBP | AAP (0.7 psi) | SFC |
| C16 | | | | | PSXM sample, no surface-crosslinking or additives | | | | | | | 31.6 | | | | |
| C17 | 1% | 3% | — | — | — | 180° C. | 30 | — | — | — | — | 27.8 | 22.8 | 15 | 24.6 | 46 |
| C18 | 1% | 3% | — | — | — | 170° C. | 90 | — | — | — | — | 27.6 | 23.5 | 15 | 25.1 | 69 |
| 101 | 1% | 3% | — | 0.3% | — | 180° C. | 30 | — | — | — | — | 27.6 | 23.3 | 11 | 25.0 | 59 |
| 102 | 1% | 3% | — | 0.3% | — | 170° C. | 90 | — | — | — | — | 28.2 | 23.8 | 9 | 25.3 | 54 |
| 103 | 1% | 3% | — | — | 0.3% | 180° C. | 30 | — | — | — | — | 27.8 | 23.0 | 22 | 24.2 | 58 |
| 104 | 1% | 3% | — | — | 0.3% | 170° C. | 90 | — | — | — | — | 27.0 | 22.6 | 24 | 24.2 | 73 |
| 105 | 1% | 3% | 0.5% | — | — | 180° C. | 30 | — | — | — | — | 27.1 | 21.0 | 98 | 22.3 | 105 |
| 106 | 1% | 3% | 0.5% | — | — | 170° C. | 90 | — | — | — | — | 27.5 | 21.1 | 105 | 22.3 | 151 |
| 107 | 1% | 3% | 0.5% | 0.3% | — | 180° C. | 30 | — | — | — | — | 28.1 | 20.9 | 118 | 22.2 | — |
| 108 | 1% | 3% | 0.5% | 0.3% | — | 170° C. | 90 | — | — | — | — | 28.4 | 20.9 | 157 | 22.2 | — |
| 109 | 1% | 3% | 0.5% | — | 0.3% | 180° C. | 30 | — | — | — | — | 27.4 | 21.2 | 140 | 22.5 | — |
| 110 | 1% | 3% | 0.5% | — | 0.3% | 170° C. | 90 | — | — | — | — | 27.8 | 20.6 | 153 | 22.5 | — |
| 111 | 1% | 3% | 0.5% | 0.15% | 0.15% | 180° C. | 30 | — | — | — | — | 27.8 | 21.5 | 112 | 22.5 | — |
| 112 | 1% | 3% | 0.5% | 0.15% | 0.15% | 170° C. | 90 | — | — | — | — | 28.4 | 20.5 | 101 | 22.1 | — |
| 113 | 1% | 3% | — | — | — | 180° C. | 30 | — | 0.5% | — | — | 27.9 | 19.7 | 73 | 22.5 | 73 |
| 114 | 1% | 3% | — | — | — | 170° C. | 90 | — | 0.5% | — | — | 27.7 | 20.7 | 78 | 22.4 | 73 |
| 115 | 1% | 3% | — | — | — | 180° C. | 30 | 4% | 0.5% | 0.3% | — | 26.6 | 19.8 | 76 | 21.5 | — |
| 116 | 1% | 3% | — | — | — | 170° C. | 90 | 4% | 0.5% | 0.3% | — | 26.5 | 19.7 | 87 | 21.1 | — |
| 117 | 1% | 3% | — | — | — | 180° C. | 30 | 4% | 0.5% | — | 0.3% | 26.7 | 19.6 | 88 | 21.8 | — |
| 118 | 1% | 3% | — | — | — | 170° C. | 90 | 4% | 0.5% | — | 0.3% | 26.4 | 19.3 | 113 | 21.3 | — |
| 119 | 1% | 3% | — | — | — | 180° C. | 30 | 4% | 0.5% | 0.15% | 0.15% | 26.6 | 19.6 | 66 | 21.2 | — |
| 120 | 1% | 3% | — | — | — | 170° C. | 90 | 4% | 0.5% | 0.15% | 0.15% | 26.8 | 19.3 | 89 | 21.5 | — |

TABLE 7

Comparative Examples C19-C21 and Examples 121-140
0.3 wt. % of Internal Crosslinker 7 (1 molDAA + 1 molAGE + 0.5 molPO) was added to the solution as set forth in making the Particulate Superabsorbent Polymer Composition and the resulting particulate superabsorbent polymer was surface crosslinked and surface treated as set forth in Table 7 to form Examples 121-140 of the particulate superabsorbent polymer composition.

| | Pre-Treatment before SX | | | | SX step | | Post-treatment after SX | | | | Properties | | | | |
|---|---|---|---|---|---|---|---|---|---|---|---|---|---|---|---|
| No. | EC | Water | Silica | Al-lactate | Al-Sulfate | Temperature | Time min | Water | Silica | Al-lactate | Al-Sulfate | CRC | AUL (0.9 psi) | GBP | AAP (0.7 psi) | SFC |
| C19 | | | | | PSXM sample, no surface-crosslinking or additives | | | | | | | 32.9 | | | | |
| C20 | 1% | 3% | — | — | — | 180° C. | 30 | — | — | — | — | 28.2 | 23.1 | 11 | 24.5 | 43 |
| C21 | 1% | 3% | — | — | — | 170° C. | 90 | — | — | — | — | 28.3 | 22.9 | 13 | 24.0 | 49 |
| 121 | 1% | 3% | — | 0.3% | — | 180° C. | 30 | — | — | — | — | 28.3 | 22.6 | 7 | 24.1 | 40 |
| 122 | 1% | 3% | — | 0.3% | — | 170° C. | 90 | — | — | — | — | 28.8 | 24.0 | 7 | 24.8 | 52 |
| 123 | 1% | 3% | — | — | 0.3% | 180° C. | 30 | — | — | — | — | 28.1 | 22.3 | 26 | 23.6 | 63 |
| 124 | 1% | 3% | — | — | 0.3% | 170° C. | 90 | — | — | — | — | 28.2 | 22.5 | 27 | 24.1 | 80 |
| 125 | 1% | 3% | 0.5% | — | — | 180° C. | 30 | — | — | — | — | 28.6 | 20.0 | 58 | 21.3 | 84 |
| 126 | 1% | 3% | 0.5% | — | — | 170° C. | 90 | — | — | — | — | 28.0 | 20.3 | 90 | 20.6 | 136 |
| 127 | 1% | 3% | 0.5% | 0.3% | — | 180° C. | 30 | — | — | — | — | 28.2 | 18.1 | 52 | 21.0 | — |
| 128 | 1% | 3% | 0.5% | 0.3% | — | 170° C. | 90 | — | — | — | — | 28.1 | 19.6 | 106 | 21.5 | — |
| 129 | 1% | 3% | 0.5% | — | 0.3% | 180° C. | 30 | — | — | — | — | 28.0 | 19.0 | 65 | 21.9 | — |
| 130 | 1% | 3% | 0.5% | — | 0.3% | 170° C. | 90 | — | — | — | — | 28.1 | 20.1 | 95 | 22.2 | — |
| 131 | 1% | 3% | 0.5% | 0.15% | 0.15% | 180° C. | 30 | — | — | — | — | 27.8 | 18.7 | 90 | 21.1 | — |
| 132 | 1% | 3% | 0.5% | 0.15% | 0.15% | 170° C. | 90 | — | — | — | — | 28.8 | 19.5 | 89 | 21.5 | — |
| 133 | 1% | 3% | — | — | — | 180° C. | 30 | — | 0.5% | — | — | 28.1 | 19.9 | 71 | 21.7 | 58 |
| 134 | 1% | 3% | — | — | — | 170° C. | 90 | — | 0.5% | — | — | 28.4 | 20.0 | 47 | 22.3 | 72 |
| 135 | 1% | 3% | — | — | — | 180° C. | 30 | 4% | 0.5% | 0.3% | — | 27.0 | 19.1 | 54 | 20.9 | — |
| 136 | 1% | 3% | — | — | — | 170° C. | 90 | 4% | 0.5% | 0.3% | — | 27.1 | 18.4 | 68 | 21.0 | — |
| 137 | 1% | 3% | — | — | — | 180° C. | 30 | 4% | 0.5% | — | 0.3% | 27.0 | 19.2 | 60 | 21.4 | — |
| 138 | 1% | 3% | — | — | — | 170° C. | 90 | 4% | 0.5% | — | 0.3% | 27.4 | 19.3 | 83 | 21.4 | — |
| 139 | 1% | 3% | — | — | — | 180° C. | 30 | 4% | 0.5% | 0.15% | 0.15% | 27.4 | 19.3 | 38 | 21.6 | — |
| 140 | 1% | 3% | — | — | — | 170° C. | 90 | 4% | 0.5% | 0.15% | 0.15% | 27.3 | 19.3 | 51 | 21.8 | — |

TABLE 8

Comparative Examples C22-C24 and Examples 141-160
0.3 wt. % of Internal Crosslinker 8 (DAA + 1 AGE + 0.5 PO and 0.035% SR454) was added to the solution as set forth in making the Particulate Superabsorbent Polymer Composition and the resulting particulate superabsorbent polymer was surface crosslinked and surface treated as set forth in Table 8 to form Examples 141-160 of the particulate superabsorbent polymer composition.

| | Pre-Treatment before SX | | | | SX step | | Post-treatment after SX | | | | Properties | | | | |
|---|---|---|---|---|---|---|---|---|---|---|---|---|---|---|---|
| No. | EC | Water | Silica | Al-lactate | Al-Sulfate | Temperature | Time min | Water | Silica | Al-lactate | Al-Sulfate | CRC | AUL (0.9 psi) | GBP | AAP (0.7 psi) | SFC |
| C22 | | | PSXM sample, no surface-crosslinking or additives | | | | | | | | | 31.8 | | | | |
| C23 | 1% | 3% | — | — | — | 180° C. | 30 | — | — | — | — | 28.0 | 23.7 | 14 | 25.1 | 41 |
| C24 | 1% | 3% | — | — | — | 170° C. | 90 | — | — | — | — | 27.9 | 23.5 | 23 | 25.1 | 75 |
| 141 | 1% | 3% | — | 0.3% | — | 180° C. | 30 | — | — | — | — | 27.8 | 22.4 | 11 | 24.5 | 48 |
| 142 | 1% | 3% | — | 0.3% | — | 170° C. | 90 | — | — | — | — | 28.2 | 23.3 | 18 | 24.8 | 61 |
| 143 | 1% | 3% | — | — | 0.3% | 180° C. | 30 | — | — | — | — | 28.1 | 22.2 | 31 | 23.9 | 78 |
| 144 | 1% | 3% | — | — | 0.3% | 170° C. | 90 | — | — | — | — | 26.9 | 22.4 | 45 | 24.1 | 108 |
| 145 | 1% | 3% | 0.5% | — | — | 180° C. | 30 | — | — | — | — | 28.0 | 19.5 | 87 | 22.0 | 100 |
| 146 | 1% | 3% | 0.5% | — | — | 170° C. | 90 | — | — | — | — | 27.7 | 20.6 | 72 | 22.2 | 150 |
| 147 | 1% | 3% | 0.5% | 0.3% | — | 180° C. | 30 | — | — | — | — | 27.7 | 19.7 | 86 | 22.0 | — |
| 148 | 1% | 3% | 0.5% | 0.3% | — | 170° C. | 90 | — | — | — | — | 28.3 | 21.0 | 82 | 22.7 | — |
| 149 | 1% | 3% | 0.5% | — | 0.3% | 180° C. | 30 | — | — | — | — | 27.7 | 19.6 | 97 | 22.1 | — |
| 150 | 1% | 3% | 0.5% | — | 0.3% | 170° C. | 90 | — | — | — | — | 27.7 | 20.3 | 84 | 22.5 | — |
| 151 | 1% | 3% | 0.5% | 0.15% | 0.15% | 180° C. | 30 | — | — | — | — | 28.4 | 20.6 | 86 | 22.5 | — |
| 152 | 1% | 3% | 0.5% | 0.15% | 0.15% | 170° C. | 90 | — | — | — | — | 28.4 | 20.2 | 74 | 22.3 | — |
| 153 | 1% | 3% | — | — | — | 180° C. | 30 | — | 0.5% | — | — | 27.8 | 19.8 | 49 | 22.5 | 58 |
| 154 | 1% | 3% | — | — | — | 170° C. | 90 | — | 0.5% | — | — | 27.8 | 20.6 | 61 | 22.1 | 65 |
| 155 | 1% | 3% | — | — | — | 180° C. | 30 | 4% | 0.5% | 0.3% | — | 26.5 | 19.4 | 82 | 21.2 | — |
| 156 | 1% | 3% | — | — | — | 170° C. | 90 | 4% | 0.5% | 0.3% | — | 26.3 | 19.5 | 60 | 21.4 | — |
| 157 | 1% | 3% | — | — | — | 180° C. | 30 | 4% | 0.5% | — | 0.3% | 26.8 | 19.8 | 57 | 21.7 | — |
| 158 | 1% | 3% | — | — | — | 170° C. | 90 | 4% | 0.5% | — | 0.3% | 26.4 | 19.9 | 90 | 21.9 | — |
| 159 | 1% | 3% | — | — | — | 180° C. | 30 | 4% | 0.5% | 0.15% | 0.15% | 26.8 | 19.1 | 62 | 21.3 | — |
| 160 | 1% | 3% | — | — | — | 170° C. | 90 | 4% | 0.5% | 0.15% | 0.15% | 26.8 | 19.7 | 69 | 21.9 | — |

TABLE 9

Comparative Examples C25-C27 and Examples 161-180
0.3 wt. % of Internal Crosslinker 9 (4 molAGE/1 molHMDA) was added to the solution as set forth in making the Particulate Superabsorbent Polymer Composition and the resulting particulate superabsorbent polymer was surface crosslinked and surface treated as set forth in Table 9 to form Examples 161-180 of the particulate superabsorbent polymer composition.

| | Pre-Treatment before SX | | | | SX step | | Post-treatment after SX | | | | Properties | | | | |
|---|---|---|---|---|---|---|---|---|---|---|---|---|---|---|---|
| No. | EC | Water | Silica | Al-lactate | Al-Sulfate | Temperature | Time min | Water | Silica | Al-lactate | Al-Sulfate | CRC | AUL (0.9 psi) | GBP | AAP (0.7 psi) | SFC |
| C25 | | | PSXM sample, no surface-crosslinking or additives | | | | | | | | | 32.3 | | | | |
| C26 | 1% | 3% | — | — | — | 180° C. | 30 | — | — | — | — | 27.2 | 23.5 | 10 | 24.4 | 33 |
| C27 | 1% | 3% | — | — | — | 170° C. | 90 | — | — | — | — | 27.5 | 23.9 | 9 | 24.6 | 35 |
| 161 | 1% | 3% | — | 0.3% | — | 180° C. | 30 | — | — | — | — | 27.6 | 23.2 | 9 | 24.1 | 61 |
| 162 | 1% | 3% | — | 0.3% | — | 170° C. | 90 | — | — | — | — | 27.2 | 23.2 | 17 | 24.5 | 106 |
| 163 | 1% | 3% | — | — | 0.3% | 180° C. | 30 | — | — | — | — | 26.6 | 21.7 | 38 | 23.7 | 118 |
| 164 | 1% | 3% | — | — | 0.3% | 170° C. | 90 | — | — | — | — | 27.0 | 20.1 | 54 | 24.1 | 110 |
| 165 | 1% | 3% | 0.5% | — | — | 180° C. | 30 | — | — | — | — | 27.1 | 20.5 | 61 | 22.2 | 113 |
| 166 | 1% | 3% | 0.5% | — | — | 170° C. | 90 | — | — | — | — | 27.9 | 20.1 | 79 | 22.1 | 89 |
| 167 | 1% | 3% | 0.5% | 0.3% | — | 180° C. | 30 | — | — | — | — | 27.3 | 21.0 | 82 | 21.9 | — |
| 168 | 1% | 3% | 0.5% | 0.3% | — | 170° C. | 90 | — | — | — | — | 27.9 | 20.0 | 89 | 21.8 | — |
| 169 | 1% | 3% | 0.5% | — | 0.3% | 180° C. | 30 | — | — | — | — | 25.7 | 20.5 | 140 | 21.7 | — |
| 170 | 1% | 3% | 0.5% | — | 0.3% | 170° C. | 90 | — | — | — | — | 26.7 | 20.4 | 125 | 21.9 | — |
| 171 | 1% | 3% | 0.5% | 0.15% | 0.15% | 180° C. | 30 | — | — | — | — | 27.4 | 20.1 | 100 | 21.9 | — |
| 172 | 1% | 3% | 0.5% | 0.15% | 0.15% | 170° C. | 90 | — | — | — | — | 27.6 | 20.2 | 91 | 22.0 | — |
| 173 | 1% | 3% | — | — | — | 180° C. | 30 | — | 0.5% | — | — | 27.1 | 19.5 | 66 | 21.7 | 108 |
| 174 | 1% | 3% | — | — | — | 170° C. | 90 | — | 0.5% | — | — | 27.6 | 20.1 | 60 | 22.0 | 110 |
| 175 | 1% | 3% | — | — | — | 180° C. | 30 | 4% | 0.5% | 0.3% | — | 26.6 | 20.3 | 49 | 21.4 | — |
| 176 | 1% | 3% | — | — | — | 170° C. | 90 | 4% | 0.5% | 0.3% | — | 26.9 | 20.4 | 48 | 21.4 | — |
| 177 | 1% | 3% | — | — | — | 180° C. | 30 | 4% | 0.5% | — | 0.3% | 26.5 | 20.0 | 62 | 21.6 | — |
| 178 | 1% | 3% | — | — | — | 170° C. | 90 | 4% | 0.5% | — | 0.3% | 27.0 | 20.6 | 64 | 21.7 | — |
| 179 | 1% | 3% | — | — | — | 180° C. | 30 | 4% | 0.5% | 0.15% | 0.15% | 26.6 | 20.3 | 43 | 21.4 | — |
| 180 | 1% | 3% | — | — | — | 170° C. | 90 | 4% | 0.5% | 0.15% | 0.15% | 27.0 | 20.7 | 46 | 21.5 | — |

TABLE 10

Comparative Examples C28-C30 and Examples 181-200
0.3 wt. % of Internal Crosslinker 10 (4 molAGE/1 molHMDA and 0.035% SR 454) was added to the solution as set forth in making the Particulate Superabsorbent Polymer Composition and the resulting particulate superabsorbent polymer was surface crosslinked and surface treated as set forth in Table 10 to form Examples 181-200 of the particulate superabsorbent polymer composition.

| | Pre-Treatment before SX | | | | SX step | | Post-treatment after SX | | | | Properties | | | | |
|---|---|---|---|---|---|---|---|---|---|---|---|---|---|---|---|
| No. | EC | Water | Silica | Al-lactate | Al-Sulfate | Temperature | Time min | Water | Silica | Al-lactate | Al-Sulfate | CRC | AUL (0.9 psi) | GBP | AAP (0.7 psi) | SFC |
| C28 | | | PSXM sample, no surface-crosslinking or additives | | | | | | | | | 32.9 | | | | |
| C29 | 1% | 3% | — | — | — | 180° C. | 30 | — | — | — | — | 28.0 | 21.7 | 6 | 23.9 | 26 |
| C30 | 1% | 3% | — | — | — | 170° C. | 90 | — | — | — | — | 27.9 | 23.3 | 8 | 24.6 | 31 |
| 181 | 1% | 3% | — | 0.3% | — | 180° C. | 30 | — | — | — | — | 28.2 | 24.4 | 9 | 24.4 | 32 |
| 182 | 1% | 3% | — | 0.3% | — | 170° C. | 90 | — | — | — | — | 27.5 | 23.9 | 11 | 24.3 | 50 |
| 183 | 1% | 3% | — | — | 0.3% | 180° C. | 30 | — | — | — | — | 27.6 | 24.2 | 29 | 24.1 | 63 |
| 184 | 1% | 3% | — | — | 0.3% | 170° C. | 90 | — | — | — | — | 27.6 | 23.7 | 32 | 24.4 | 58 |
| 185 | 1% | 3% | 0.5% | — | — | 180° C. | 30 | — | — | — | — | 27.7 | 21.1 | 80 | 22.5 | 77 |
| 186 | 1% | 3% | 0.5% | — | — | 170° C. | 90 | — | — | — | — | 27.7 | 23.3 | 102 | 22.0 | 98 |
| 187 | 1% | 3% | 0.5% | 0.3% | — | 180° C. | 30 | — | — | — | — | 27.5 | 21.6 | 98 | 21.9 | — |
| 188 | 1% | 3% | 0.5% | 0.3% | — | 170° C. | 90 | — | — | — | — | 27.7 | 22.0 | 112 | 21.2 | — |
| 189 | 1% | 3% | 0.5% | — | 0.3% | 180° C. | 30 | — | — | — | — | 26.4 | 20.3 | 92 | 21.6 | — |
| 190 | 1% | 3% | 0.5% | — | 0.3% | 170° C. | 90 | — | — | — | — | 27.4 | 22.6 | 97 | 21.9 | — |
| 191 | 1% | 3% | 0.5% | 0.15% | 0.15% | 180° C. | 30 | — | — | — | — | 27.2 | 21.6 | 94 | 21.2 | — |
| 192 | 1% | 3% | 0.5% | 0.15% | 0.15% | 170° C. | 90 | — | — | — | — | 27.2 | 20.6 | 98 | 22.2 | — |
| 193 | 1% | 3% | — | — | — | 180° C. | 30 | — | 0.5% | — | — | 27.2 | 19.4 | 73 | 21.7 | 101 |
| 194 | 1% | 3% | — | — | — | 170° C. | 90 | — | 0.5% | — | — | 27.6 | 20.2 | 98 | 22.5 | 100 |
| 195 | 1% | 3% | — | — | — | 180° C. | 30 | 4% | 0.5% | 0.3% | — | 27.1 | 19.4 | 51 | 20.7 | — |
| 196 | 1% | 3% | — | — | — | 170° C. | 90 | 4% | 0.5% | 0.3% | — | 27.3 | 19.6 | 59 | 21.6 | — |
| 197 | 1% | 3% | — | — | — | 180° C. | 30 | 4% | 0.5% | — | 0.3% | 26.8 | 20.5 | 55 | 21.7 | — |
| 198 | 1% | 3% | — | — | — | 170° C. | 90 | 4% | 0.5% | — | 0.3% | 27.0 | 19.4 | 47 | 21.7 | — |
| 199 | 1% | 3% | — | — | — | 180° C. | 30 | 4% | 0.5% | 0.15% | 0.15% | 27.5 | 18.9 | 47 | 21.1 | — |
| 200 | 1% | 3% | — | — | — | 170° C. | 90 | 4% | 0.5% | 0.15% | 0.15% | 27.3 | 20.2 | 45 | 21.2 | — |

TABLE 11

Comparative Examples C31-C33 and Examples 201-220
0.3 wt. % of Internal Crosslinker 11 (4 molAGE/1 molHMDA + 0.5 molPO) was added to the solution as set forth in making the Particulate Superabsorbent Polymer Composition and the resulting particulate superabsorbent polymer was surface crosslinked and surface treated as set forth in Table 11 to form Examples 201-220 of the particulate superabsorbent polymer composition.

| | Pre-Treatment before SX | | | | SX step | | Post-treatment after SX | | | | Properties | | | | |
|---|---|---|---|---|---|---|---|---|---|---|---|---|---|---|---|
| No. | EC | Water | Silica | Al-lactate | Al-Sulfate | Temperature | Time min | Water | Silica | Al-lactate | Al-Sulfate | CRC | AUL (0.9 psi) | GBP | AAP (0.7 psi) | SFC |
| C31 | | | PSXM sample, no surface-crosslinking or additives | | | | | | | | | 32.7 | | | | |
| C32 | 1% | 3% | — | — | — | 180° C. | 30 | — | — | — | — | 27.3 | 22.5 | 11 | 24.6 | 26 |
| C33 | 1% | 3% | — | — | — | 170° C. | 90 | — | — | — | — | 27.7 | 22.7 | 9 | 24.1 | 31 |
| 201 | 1% | 3% | — | 0.3% | — | 180° C. | 30 | — | — | — | — | 27.3 | 23.8 | 12 | 24.1 | 32 |
| 202 | 1% | 3% | — | 0.3% | — | 170° C. | 90 | — | — | — | — | 27.6 | 23.3 | 12 | 24.4 | 50 |
| 203 | 1% | 3% | — | — | 0.3% | 180° C. | 30 | — | — | — | — | 26.2 | 21.7 | 48 | 23.4 | 63 |
| 204 | 1% | 3% | — | — | 0.3% | 170° C. | 90 | — | — | — | — | 27.0 | 22.4 | 76 | 23.9 | 58 |
| 205 | 1% | 3% | 0.5% | — | — | 180° C. | 30 | — | — | — | — | 26.7 | 20.0 | 150 | 21.6 | 77 |
| 206 | 1% | 3% | 0.5% | — | — | 170° C. | 90 | — | — | — | — | 27.1 | 19.9 | 170 | 21.8 | 98 |
| 207 | 1% | 3% | 0.5% | 0.3% | — | 180° C. | 30 | — | — | — | — | 26.7 | 20.2 | 173 | 21.8 | — |
| 208 | 1% | 3% | 0.5% | 0.3% | — | 170° C. | 90 | — | — | — | — | 27.1 | 19.8 | 158 | 21.5 | — |
| 209 | 1% | 3% | 0.5% | — | 0.3% | 180° C. | 30 | — | — | — | — | 26.6 | 20.4 | 188 | 21.5 | — |
| 210 | 1% | 3% | 0.5% | — | 0.3% | 170° C. | 90 | — | — | — | — | 27.4 | 20.0 | 164 | 21.7 | — |
| 211 | 1% | 3% | 0.5% | 0.15% | 0.15% | 180° C. | 30 | — | — | — | — | 26.1 | 19.4 | 167 | 21.0 | — |
| 212 | 1% | 3% | 0.5% | 0.15% | 0.15% | 170° C. | 90 | — | — | — | — | 26.9 | 19.8 | 165 | 21.8 | — |
| 213 | 1% | 3% | — | — | — | 180° C. | 30 | — | 0.5% | — | — | 27.2 | 19.4 | 73 | 21.7 | 101 |
| 214 | 1% | 3% | — | — | — | 170° C. | 90 | — | 0.5% | — | — | 27.6 | 20.2 | 98 | 22.5 | 100 |
| 215 | 1% | 3% | — | — | — | 180° C. | 30 | 4% | 0.5% | 0.3% | — | 26.5 | 19.7 | 61 | 21.5 | — |
| 216 | 1% | 3% | — | — | — | 170° C. | 90 | 4% | 0.5% | 0.3% | — | 27.0 | 19.9 | 76 | 21.3 | — |
| 217 | 1% | 3% | — | — | — | 180° C. | 30 | 4% | 0.5% | — | 0.3% | 27.0 | 20.2 | 82 | 21.7 | — |
| 218 | 1% | 3% | — | — | — | 170° C. | 90 | 4% | 0.5% | — | 0.3% | 27.5 | 20.1 | 88 | 21.6 | — |
| 219 | 1% | 3% | — | — | — | 180° C. | 30 | 4% | 0.5% | 0.15% | 0.15% | 26.9 | 20.1 | 54 | 21.7 | — |
| 220 | 1% | 3% | — | — | — | 170° C. | 90 | 4% | 0.5% | 0.15% | 0.15% | 27.2 | 20.1 | 61 | 21.4 | — |

TABLE 12

Comparative Examples C34-C36 and Examples 221-240
0.3 wt. % of Internal Crosslinker 12 (1 molAGE/1 molHMDA + 0.5 molPO) and 0.035% SR 454) was added to the solution as set forth in making the Particulate Superabsorbent Polymer Composition and the resulting particulate superabsorbent polymer was surface crosslinked and surface treated as set forth in Table 12 to form Examples 221-240 of the particulate superabsorbent polymer composition.

| | Pre-Treatment before SX | | | | SX step | | Post-treatment after SX | | | | Properties | | | | |
|---|---|---|---|---|---|---|---|---|---|---|---|---|---|---|---|
| No. | EC | Water | Silica | Al-lactate | Al-Sulfate | Temperature | Time min | Water | Silica | Al-lactate | Al-Sulfate | CRC | AUL (0.9 psi) | GBP | AAP (0.7 psi) | SFC |
| C34 | | | | | PSXM sample, no surface-crosslinking or additives | | | | | | | 32 | | | | |
| C35 | 1% | 3% | — | — | — | 180° C. | 30 | — | — | — | — | 27.3 | 23.2 | 14 | 24.2 | 47 |
| C36 | 1% | 3% | — | — | — | 170° C. | 90 | — | — | — | — | 27.3 | 23.1 | 11 | 24.3 | 39 |
| 221 | 1% | 3% | — | 0.3% | — | 180° C. | 30 | — | — | — | — | 27.7 | 22.6 | 9 | 23.4 | 43 |
| 222 | 1% | 3% | — | 0.3% | — | 170° C. | 90 | — | — | — | — | 27.5 | 23.4 | 13 | 24.3 | 61 |
| 223 | 1% | 3% | — | — | 0.3% | 180° C. | 30 | — | — | — | — | 26.7 | 22.3 | 32 | 23.5 | 87 |
| 224 | 1% | 3% | — | — | 0.3% | 170° C. | 90 | — | — | — | — | 27.0 | 22.9 | 31 | 24.3 | 89 |
| 225 | 1% | 3% | 0.5% | — | — | 180° C. | 30 | — | — | — | — | 26.7 | 20.3 | 79 | 21.2 | 112 |
| 226 | 1% | 3% | 0.5% | — | — | 170° C. | 90 | — | — | — | — | 27.2 | 21.0 | 101 | 22.2 | 147 |
| 227 | 1% | 3% | 0.5% | 0.3% | — | 180° C. | 30 | — | — | — | — | 27.2 | 20.8 | 117 | 21.7 | — |
| 228 | 1% | 3% | 0.5% | 0.3% | — | 170° C. | 90 | — | — | — | — | 27.1 | 20.5 | 88 | 21.7 | — |
| 229 | 1% | 3% | 0.5% | — | 0.3% | 180° C. | 30 | — | — | — | — | 27.3 | 20.5 | 87 | 21.7 | — |
| 230 | 1% | 3% | 0.5% | — | 0.3% | 170° C. | 90 | — | — | — | — | 26.8 | 20.9 | 106 | 22.0 | — |
| 231 | 1% | 3% | 0.5% | 0.15% | 0.15% | 180° C. | 30 | — | — | — | — | 27.6 | 20.0 | 75 | 21.7 | — |
| 232 | 1% | 3% | 0.5% | 0.15% | 0.15% | 170° C. | 90 | — | — | — | — | 27.2 | 20.6 | 73 | 22.1 | — |
| 233 | 1% | 3% | — | — | — | 180° C. | 30 | — | 0.5% | — | — | 27.3 | 19.3 | 69 | 22.4 | 85 |
| 234 | 1% | 3% | — | — | — | 170° C. | 90 | — | 0.5% | — | — | 27.3 | 20.5 | 84 | 22.9 | 109 |
| 235 | 1% | 3% | — | — | — | 180° C. | 30 | 4% | 0.5% | 0.3% | — | 26.4 | 20.2 | 42 | 21.3 | — |
| 236 | 1% | 3% | — | — | — | 170° C. | 90 | 4% | 0.5% | 0.3% | — | 26.5 | 19.9 | 55 | 21.3 | — |
| 237 | 1% | 3% | — | — | — | 180° C. | 30 | 4% | 0.5% | — | 0.3% | 25.9 | 20.2 | 68 | 21.3 | — |
| 238 | 1% | 3% | — | — | — | 170° C. | 90 | 4% | 0.5% | — | 0.3% | 26.1 | 20.6 | 77 | 21.2 | — |
| 239 | 1% | 3% | — | — | — | 180° C. | 30 | 4% | 0.5% | 0.15% | 0.15% | 26.2 | 20.0 | 58 | 21.3 | — |
| 240 | 1% | 3% | — | — | — | 170° C. | 90 | 4% | 0.5% | 0.15% | 0.15% | 26.6 | 20.1 | 67 | 21.3 | — |

Notwithstanding that the numerical ranges and parameters setting forth the broad scope of the invention are approximations, the numerical values set forth in the specific examples are reported as precisely as possible. Other than in the operating examples, or where otherwise indicated, all numbers expressing quantities of ingredients, reaction conditions, and so forth used in the specification and claims are to be understood as being modified in all instances by the term "about". Any numerical value, however, inherently contain certain errors necessarily resulting from the standard deviation found in their respective testing measurements.

What is claimed is:

1. A particulate superabsorbent polymer composition having increased permeability wherein the particulate superabsorbent polymer comprises
   a) a polymerizable monomer wherein the monomer is selected from unsaturated acid groups-containing monomers, ethylenically unsaturated carboxylic acid anhydride, salts, or derivatives thereof;
   b) an internal crosslinker composition that is the reaction product selected from
   (i) saturated amines and/or saturated polyamines with ethylenically unsaturated glycidyl compounds and/or ethylenically unsaturated polyglycidyl compounds, or
   (ii) ethylenically unsaturated amines and/or ethylenically unsaturated polyamines with saturated glycidyl compounds and/or saturated polyglycidyl compounds, or
   (iii) ethylenically unsaturated amines and/or ethylenically unsaturated polyamines with ethylenically unsaturated glycidyl compounds and/or ethylenically unsaturated polyglycidyl compounds;
   wherein components a) and b) are polymerized and granulated to form particulate superabsorbent polymer which has a particle surface, wherein at least 40 wt % of the particulate superabsorbent polymer has a particle size from 300 μm to 600 μm; and
   c) from 0.01 to 5 wt % based on the dry superabsorbent polymer composition powder weight of a surface cross-linking agent applied to the particle surface;
   wherein the particulate superabsorbent polymer composition has a Centrifuge Retention Capacity of from 20 g/g to 40 g/g as determined by the Centrifuge Retention Capacity Test set forth herein, and a gel bed permeability of at least 5 Darcy or more as determined by the Gel Bed Permeability Test set forth herein.

2. The particulate superabsorbent polymer composition according to claim 1 further comprising d) from 0.01 wt % to 5 wt % based on the dry particulate superabsorbent polymer composition powder weight of an insoluble, inorganic powder and/or from 0.01 to 5 wt % based on dry polymer powder weight of a multivalent metal salt; wherein the particulate superabsorbent polymer composition has a gel bed permeability of from 10 Darcy to 200 Darcy as determined by the Gel Bed Permeability Test set forth herein.

3. The particulate superabsorbent polymer composition according to claim 1 further comprising e) from 0.01 wt % to 5 wt % based on the dry superabsorbent polymer composition powder weight of a multivalent metal salt.

4. The particulate superabsorbent polymer composition according to claim 1 further comprising f) from 0.01 to 0.5 wt. % based on the dry superabsorbent polymer composition weight of a thermoplastic polymer.

5. The particulate superabsorbent polymer composition according to claim 1 further comprising g) from 0.01 to 1wt % based on the dry particulate superabsorbent polymer composition weight of a cationic polymer.

6. The particulate superabsorbent polymer composition of claim 1 comprises from 0.01 to 1wt % based on the polymerizable monomer of the internal crosslinker composition and from 0.001 to 1.0 wt % based on the polymerizable monomer of a second internal crosslinker composition.

7. The particulate superabsorbent polymer composition of claim 1 wherein the ethylenically unsaturated glycidyl compounds and/or ethylenically unsaturated polyglycidyl compounds are selected from ethylene glycol monoglycidyl ether and the related C1-C6-alkyl ethers or esters thereof; glycidol, ethylene oxide, propylene oxide, (meth)allyl glycidyl ethers, polyethylene glycol monoglycidyl ethers and the related C1-C6-alkyl ethers or esters thereof; vinyl glycidyl ethers, glycidyl(meth)acrylates, glycidyl(meth)allyl ethers, or 1-halogen-2,3-epoxypropane; ethylene glycol or polyglycol diglycidyl ethers; glycerol, trimethylolpropane, or pentaerythritol triglycidyl ethers; polyglycerol polyglycidyl ethers, sorbitol polyglycidyl ethers, or their mixtures thereof.

8. The particulate superabsorbent polymer composition of claim 1 wherein the ethylenically unsaturated glycidyl compounds and/or ethylenically unsaturated polyglycidyl compounds comprise glycidyl compounds that comprise polyethylene glycol chains having up to 45 ethylene glycol units, or up to 20 ethylene glycol units, or up to 12 ethylene glycol units.

9. The particulate superabsorbent polymer composition of claim 1 wherein the ethylenically unsaturated glycidyl compounds and/or ethylenically unsaturated polyglycidyl compounds are selected from (meth)allyl glycidyl ethers or glycidyl (meth)acrylate.

10. The particulate superabsorbent polymer composition of claim 1 wherein the saturated amines and/or saturated polyamines are selected from (mono, di and poly)aminoalkanes, (mono, di and poly)aminopolyethers, allylamine, alkyl(meth)allylamines, e.g., methyl allylamine, methyl methallylamine, ethyl methallylamine, and ethyl allylamine; methyl-, ethyl-, propyl- and butylamine, diallylamine, dimethallylamine, aniline, ethylenediamine, diethylenetriamine, hexamethylenediamine, trimethylhexamethylenediamine, neopentane diamine, 1,2-propylenediamine, 4,7-dioxadecane-1,10-diamine, 4,9-dioxadodecane-1,12-diamine, polyether diamines, polyalkylene glycol diamines, 3-amino-1-methylaminopropane, bis(3-aminopropyl)methylamine, isophorone diamine, 4,4'-diaminodicyclohexylmethane, 1-(2-aminoethyl)piperazine, o-, m-, or p-phenylenediamine, 4,4'-diaminodiphenyimethane, 1,4-diaminoanthraquinone, 2,4,6-triamino-1,3,5-triazine, aminopyridine, glucosamine, and mixtures thereof.

11. The particulate superabsorbent polymer composition according to claim 1 wherein the saturated amines and/or saturated polyamines are selected from ethylene diamine, hexamethylenediamine, diethylene triamine, or 2,2'-[1,2-ethanediylbis(oxy)]bis-ethanamine.

12. The particulate superabsorbent polymer composition according to claim 1 wherein the second internal crosslinker composition is selected from methylenebisacrylamide or -methacrylamide or ethylenebisacrylamide; esters of unsaturated mono- or polycarboxylic acids of polyols including diacrylates or triacrylates, butanediol- or ethylene glycol diacrylate or -methacrylate; trimethylolpropane triacrylate, and their alkoxylates; allyl compounds including allyl (meth)acrylate, triallyl cyanurate, maleic acid diallyl ester, polyallyl ester, tetraallyloxyethane, di- and triallylamine, tetrallylethylenediamine, allyl esters of phosphoric acid or phosphorous acid.

13. The particulate superabsorbent polymer composition according to claim 1 wherein the unsaturated, acid groups-containing monomers are selected from acrylic acid, methacrylic acid, vinyl acetic acid, vinyl sulfonic acid, methallyl sulfonic acid, and 2-acrylamido-2-methylpropane sulfonic acid.

14. The particulate superabsorbent polymer composition according to claim 1 which additionally comprises from 0 to 40 wt %, relative to the polymerizable monomers, of comonomers selected from the group consisting of (meth) acrylamide, (meth)acrylonitrile, vinyl pyrrolidone, hydroxyethyl acrylate, and vinyl acetamide.

15. The particulate superabsorbent polymer composition according to claim 1 wherein the surface crosslinking agent comprises ethylene carbonate.

16. The particulate superabsorbent polymer composition of claim 1 wherein the polymerizable monomer has a degree of neutralization from 50 mol % to 85 mol %.

17. The particulate superabsorbent polymer composition of claim 1 having a Gel Bed Permeability of from 50 Darcy to 150 Darcy as determined by the Gel Bed Permeability Test set forth herein.

18. The particulate superabsorbent polymer composition of claim 1 having an Absorbency Under Load at 0.9 psi (AUL(0.9 psi)) of from 12 g/g to 30 g/g as determined by the Absorbency Under Load(0.9 psi) Test set forth herein; or having an Absorbency Against Pressure at 0.7 psi (AAP(0.7 psi)) of from 15 g/g to 40 g/g as determined by the Absorbency At Pressure (0.7 psi) Test as set forth herein; or having a Saline Flow Conductivity of from $20 \times 10^{-7}$*cm3*s*g-1 to $200 \times 10^{-7}$*cm3*s*g-1 as determined by the Saline Flow Conductivity (SFC) Test as set forth herein.

19. A method to make particulate superabsorbent polymer composition comprising the steps of:
   a) preparing a superabsorbent polymer by the process of polymerizing of at least one monomer selected from an ethylenically unsaturated carboxylic acid, ethylenically unsaturated carboxylic acid anhydride, salts or derivatives thereof based on the superabsorbent polymer, and from 0.001% by weight to 1% by weight of an internal crosslinking composition that is the reaction product selected from
      (i) saturated amines and/or saturated polyamines with ethylenically unsaturated glycidyl compounds and/or ethylenically unsaturated polyglycidyl compounds,
      (ii) ethylenically unsaturated amines and/or ethylenically unsaturated polyamines with saturated glycidyl compounds and/or saturated polyglycidyl compounds, or
      (iii) ethylenically unsaturated amines and/or ethylenically unsaturated polyamines with ethylenically unsaturated glycidyl compounds and/or ethylenically unsaturated polyglycidyl compounds;
   b) polymerizing the superabsorbent polymer;
   c) granulating the superabsorbent polymer to form particulate superabsorbent polymer wherein at least 40 wt % of the particulate superabsorbent polymer has a particle size from 300 μm to 600 μm;
   d) surface crosslinking the particulate superabsorbent polymer with from 0.001 wt % to 5.0 wt % based on the dry superabsorbent polymer composition powder weight of surface crosslinking agent applied to the particle surface; and
   e) heat treating the surface crosslinked particulate superabsorbent polymer of step d) at a temperature from 150° C. to 250° C. for 20 to 120 minutes to form surface crosslinked particulate superabsorbent polymer; and
   wherein the particulate superabsorbent polymer composition has a Centrifuge Retention Capacity of from 20 g/g to 40 g/g as determined by the Centrifuge Retention Capacity Test set forth herein, and a gel bed permeability of at least 5 Darcy or more as determined by the Gel Bed Permeability Test set forth herein.

20. The method of claim 19 further comprising the step of f) surface treating the surface crosslinked particulate superabsorbent polymer composition of step e) with from 0.01 to 5 wt % based on the dry superabsorbent polymer composition powder weight of an insoluble, inorganic powder and/or from 0.01 wt % to 5 wt % based on the dry superabsorbent polymer composition weight of a multivalent metal salt wherein the superabsorbent polymer has a Gel Bed Permeability of from 20 Darcy to 200 Darcy as determined by the Gel Bed Permeability Test set forth herein.

21. The method of claim 19 wherein further comprising the step of g) surface treating the particulate superabsorbent polymer composition with from 0.01 wt % to 5 wt % based on the dry particulate superabsorbent polymer composition weight of from 0.01 wt % to 5 wt % based on the dry particulate superabsorbent polymer composition powder weight of a multivalent metal salt wherein the superabsorbent polymer has a Gel Bed Permeability of from 20 Darcy to 200 Darcy as determined by the Gel Bed Permeability Test set forth herein.

22. The method of claim 19 wherein the ethylenically unsaturated glycidyl compounds and/or ethylenically unsaturated polyglycidyl compounds are selected from ethylene glycol monoglycidyl ether and the related C1-C6-alkyl ethers or esters thereof; glycidol, ethylene oxide, propylene oxide, (meth)allyl glycidyl ethers, polyethylene glycol monoglycidyl ethers and the related C1-C6-alkyl ethers or esters thereof; vinyl glycidyl ethers, glycidyl(meth)acrylates, glycidyl(meth)allyl ethers, or 1-halogen-2,3-epoxypropane; ethylene glycol or polyglycol diglycidyl ethers; glycerol, trimethylolpropane, or pentaerythritol triglycidyl ethers; polyglycerol polyglycidyl ethers, sorbitol polyglycidyl ethers, or their mixtures thereof.

23. The method of claim 19 wherein the ethylenically unsaturated glycidyl compounds and/or ethylenically unsaturated polyglycidyl compounds comprise glycidyl compounds that comprise polyethylene glycol chains having up to 45 ethylene glycol units, or up to 20 ethylene glycol units, or up to 12 ethylene glycol units.

24. The method of claim 19 wherein the ethylenically unsaturated glycidyl compounds and/or ethylenically unsaturated polyglycidyl compounds are selected from (meth)allyl glycidyl ether or glycidyl (meth)acrylate.

25. The method of claim 19 wherein the amine compounds are selected from (mono, di and poly)aminoalkanes, (mono, di and poly)aminopolyethers, allylamine, alkyl(meth)allylamines, e.g., methyl allylamine, methyl methallylamine, ethyl methallylamine, and ethyl allylamine; methyl-, ethyl-, propyl- and butylamine, diallylamine, dimethallylamine, aniline, ethylenediamine, diethylenetriamine, hexamethylenediamine, trimethylhexamethylenediamine, neopentane diamine, 1,2-propylenediamine, 4,7-dioxadecane-1,10-diamine, 4,9-dioxadodecane-1,12-diamine, polyether diamines, polyalkylene glycol diamines, 3-amino-1-methylaminopropane, bis(3-aminopropyl)methylamine, isophorone diamine, 4,4'-diaminodicyclohexylmethane, 1-(2-aminoethyl)piperazine, o-, m-, or p-phenylenediamine, 4,4'-diaminodiphenyimethane, 1,4-diaminoanthraquinone, 2,4,6-triamino-1,3,5-triazine, aminopyridine, glucosamine, and mixtures thereof.

26. The method of claim 19 wherein the amine compounds are selected from ethylene diamine, diallylamine, hexamethylenediamine, diethylene triamine, or 2,2'-[1,2-ethanediylbis(oxy)]bis-ethanamine.

27. A method to make particulate superabsorbent polymer composition comprising the steps of:

a) preparing a superabsorbent polymer by the process of polymerizing at least one monomer selected from an ethylenically unsaturated carboxylic acid, ethylenically unsaturated carboxylic acid anhydride, salts or derivatives thereof based on the superabsorbent polymer, and from 0.001 wt % to 1 wt % based on the monomer of an internal crosslinking composition that is the reaction product selected from
  (i) saturated amines and/or saturated polyamines with ethylenically unsaturated glycidyl compounds and/or ethylenically unsaturated polyglycidyl compounds,
  (ii) ethylenically unsaturated amines and/or ethylenically unsaturated polyamines with saturated glycidyl compounds and/or saturated polyglycidyl compounds, or
  (iii) ethylenically unsaturated amines and/or ethylenically unsaturated polyamines with ethylenically unsaturated glycidyl compounds and/or ethylenically unsaturated polyglycidyl compounds;
b) polymerizing the superabsorbent polymer;
c) granulating the superabsorbent polymer to form particulate superabsorbent polymer wherein at least 40 wt % of the particulate superabsorbent polymer has a particle size from 300 μm to 600 μm;
d) surface treating the surface crosslinked particulate superabsorbent polymer of step c) with from 0.01 to 5 wt % based on the dry superabsorbent polymer composition weight of an insoluble, inorganic powder and/or from 0.01 to 5 wt % based on the dry superabsorbent polymer composition weight of a multivalent metal salt;
e) surface crosslinking the particulate superabsorbent polymer with from 0.001 wt % to 5.0 wt % based on the dry superabsorbent polymer composition powder weight of surface crosslinking agent applied to the particle surface; and
f) heat treating the surface crosslinked particulate superabsorbent polymer of step e) at a temperature from 150° C. to 250° C. for from 20 to 120 minutes to form surface crosslinked particulate superabsorbent polymer; and
wherein the particulate superabsorbent polymer composition has a Centrifuge Retention Capacity of 20 g/g to 40 g/g as determined by the Centrifuge Retention Capacity Test set forth herein, and a Gel Bed Permeability of at least 5 Darcy or more as determined by the Gel Bed Permeability Test set forth herein.

28. The method of claim 27 comprising the step of g) surface treating the surface crosslinked particulate superabsorbent polymer of step f) with from 0.01 to 5 wt % based on the dry superabsorbent polymer composition powder weight of an insoluble, inorganic powder and/or from 0.01 to 5 wt % based on the dry superabsorbent polymer composition powder weight of a multivalent metal salt, wherein the particulate superabsorbent polymer composition has a Gel Bed Permeability of from 20 Darcy to 200 Darcy as determined by the Gel Bed Permeability Test set forth herein.

29. The method of claim 28 wherein the ethylenically unsaturated glycidyl compounds and/or ethylenically unsaturated polyglycidyl compounds comprise glycidyl compounds that comprise polyethylene glycol chains having up to 45 ethylene glycol units, or up to 20 ethylene glycol units, or up to 12 ethylene glycol units.

30. The method of claim 27 wherein the ethylenically unsaturated glycidyl and/or ethylenically unsaturated polyglycidyl compounds are selected from (meth)allyl glycidyl ethers or glycidyl (meth)acrylate.

31. The method of claim 27 wherein the amine compounds are selected from (mono, di and poly)aminoalkanes, (mono, di and poly)aminopolyethers, allylamine, alkyl(meth)allylamines, e.g., methyl allylamine, methyl methallylamine, ethyl methallylamine, and ethyl allylamine; methyl-, ethyl-, propyl- and butylamine, diallylamine, dimethallylamine, aniline, ethylenediamine, diethylenetriamine, hexamethylenediamine, trimethylhexamethylenediamine, neopentane diamine, 1,2-propylenediamine, 4,7-dioxadecane-1,10-diamine, 4,9-dioxadodecane-1,12-diamine, polyether diamines, polyalkylene glycol diamines, 3-amino-1-methylaminopropane, bis(3-aminopropyl)methylamine, isophorone diamine, 4,4'-diaminodicyclohexylmethane, 1-(2-aminoethyl)piperazine, o-, m-, or p-phenylenediamine, 4,4'-diaminodiphenyimethane, 1,4-diaminoanthraquinone, 2,4,6-triamino-1,3,5-triazine, aminopyridine, glucosamine, and mixtures thereof.

32. The method of claim 27 wherein the amine compounds are selected from ethylene diamine, diallylamine, hexamethylenediamine, diethylene triamine, or 2,2'-[1,2-ethanediylbis(oxy)]bis-ethanamine.

33. An absorbent article comprising: (a) a liquid pervious topsheet; (b) a liquid impervious backsheet; (c) a core positioned between (a) and (b), said core comprising 10% to 100% by weight of the particulate superabsorbent polymer composition and 0% to 90% by weight of hydrophilic fiber material; (d) optionally a tissue layer positioned directly above and below said core (c); and (e) optionally an acquisition layer positioned between (a) and (c) wherein the particulate superabsorbent polymer composition comprises i) a monomer selected from an ethylenically unsaturated carboxylic acid, ethylenically unsaturated carboxylic acid anhydride, salts or derivatives thereof, and ii) an internal crosslinker composition that is the reaction product selected from
- (α) saturated amines and/or saturated polyamines with ethylenically unsaturated glycidyl compounds and/or ethylenically unsaturated polyglycidyl compounds,
- (β) ethylenically unsaturated amines and/or ethylenically unsaturated polyamines with saturated glycidyl compounds and/or saturated polyglycidyl compounds, or
- (γ) ethylenically unsaturated amines and/or ethylenically unsaturated polyamines with ethylenically unsaturated glycidyl compounds and/or ethylenically unsaturated polyglycidyl compounds;

iii) from 0.001 wt % to 5.0 wt % based on the dry superabsorbent polymer composition powder weight of surface crosslinking agent applied to the particle surface;

wherein the particulate superabsorbent polymer composition has a Centrifuge Retention Capacity of from 20 g/g to 40 g/g as determined by the Centrifuge Retention Capacity Test set forth herein, and a gel bed permeability of at least 5 Darcy or more as determined by the Gel Bed Permeability Test set forth herein.

34. The absorbent article of claim 33 wherein the particulate superabsorbent polymer composition further comprises iv) from 0.01 to 5 wt % based on the dry superabsorbent polymer composition weight of an insoluble, inorganic powder; wherein the particulate superabsorbent polymer composition has a gel bed permeability of from 20 Darcy to 200 Darcy as determined by the Gel Bed Permeability Test set forth herein.

35. The absorbent article of claim 33 wherein the ethylenically unsaturated glycidyl compounds and/or ethylenically unsaturated polyglycidyl compounds are selected from ethylene glycol monoglycidyl ether and the related C1-C6-alkyl ethers or esters thereof; glycidol, ethylene oxide, propylene oxide, (meth)allyl glycidyl ethers, polyethylene glycol monoglycidyl ethers and the related C1-C6-alkyl ethers or esters thereof; vinyl glycidyl ethers, glycidyl(meth)acrylates, glycidyl(meth)allyl ethers, or 1-halogen-2,3-epoxypropane; ethylene glycol or polyglycol diglycidyl ethers; glycerol, trimethylolpropane, or pentaerythritol triglycidyl ethers; polyglycerol polyglycidyl ethers, sorbitol polyglycidyl ethers, or their mixtures thereof.

36. The absorbent article of claim 33 wherein the ethylenically unsaturated glycidyl and/or ethylenically unsaturated polyglycidyl compounds comprise polyethylene glycol chains having up to 45 ethylene glycol units, or up to 20 ethylene glycol units, or up to 12 ethylene glycol units.

37. The absorbent article of claim 33 wherein the ethylenically unsaturated glycidyl and/or ethylenically unsaturated polyglycidyl compounds are selected from (meth)allyl glycidyl ethers or glycidyl (meth)acrylate.

38. The absorbent article of claim 33 wherein the amine compounds are selected from (mono, di and poly)aminoalkanes, (mono, di and poly)aminopolyethers, allylamine, alkyl(meth)allylamines, e.g., methyl allylamine, methyl methallylamine, ethyl methallylamine, and ethyl allylamine; methyl-, ethyl-, propyl- and butylamine, diallyl amine, dimethallylamine, aniline, ethylenediamine, diethylenetriamine, hexamethylenediamine, trimethylhexamethylenediamine, neopentane diamine, 1,2-propylenediamine, 4,7-dioxadecane-1,10-diamine, 4,9-dioxadodecane-1,12-diamine, polyether diamines, polyalkylene glycol diamines, 3-amino-1-methylaminopropane, bis(3-aminopropyl)methylamine, isophorone diamine, 4,4'-diaminodicyclohexylmethane, 1-(2-aminoethyl)piperazine, o-, m-, or p-phenylenediamine, 4,4'-diaminodiphenyimethane, 1,4-diaminoanthraquinone, 2,4,6-triamino-1,3,5-triazine, aminopyridine, glucosamine, and mixtures thereof.

39. The absorbent article of claim 33 wherein the amine compounds are selected from ethylene diamine, hexamethylenediamine, diethylene triamine, or 2,2'-[1,2-ethanediylbis(oxy)]bis-ethanamine.

40. The absorbent article of claim 33 wherein the absorbent article is a diaper.

* * * * *